United States Patent
Gary et al.

(10) Patent No.: US 11,237,163 B2
(45) Date of Patent: Feb. 1, 2022

(54) IMMUNOASSAY CONTROLS AND THE USE THEREOF

(71) Applicant: Quidel Cardiovascular Inc., San Diego, CA (US)

(72) Inventors: Jonathan Gary, San Diego, CA (US); Scott Rongey, San Diego, CA (US); James Powell, San Diego, CA (US)

(73) Assignee: Quidel Cardiovascular Inc., San Diego, CA (US)

( * ) Notice: Subject to any disclaimer, the term of this patent is extended or adjusted under 35 U.S.C. 154(b) by 327 days.

(21) Appl. No.: 16/083,486

(22) PCT Filed: Mar. 7, 2017

(86) PCT No.: PCT/US2017/021211
§ 371 (c)(1),
(2) Date: Sep. 7, 2018

(87) PCT Pub. No.: WO2017/156038
PCT Pub. Date: Sep. 14, 2017

(65) Prior Publication Data
US 2019/0339264 A1 Nov. 7, 2019

Related U.S. Application Data

(60) Provisional application No. 62/346,347, filed on Jun. 6, 2016, provisional application No. 62/304,762, filed on Mar. 7, 2016.

(51) Int. Cl.
*G01N 33/558* (2006.01)
*C07K 16/18* (2006.01)
*G01N 33/543* (2006.01)
*G01N 33/68* (2006.01)
*G01N 33/74* (2006.01)
*G16H 40/63* (2018.01)

(52) U.S. Cl.
CPC ......... *G01N 33/558* (2013.01); *C07K 16/18* (2013.01); *G01N 33/54393* (2013.01); *G16H 40/63* (2018.01); *G01N 33/6887* (2013.01); *G01N 33/74* (2013.01); *G01N 2333/4712* (2013.01); *G01N 2410/00* (2013.01)

(58) Field of Classification Search
None
See application file for complete search history.

(56) References Cited

U.S. PATENT DOCUMENTS

| | | |
|---|---|---|
| 6,475,785 B1 | 11/2002 | Shi et al. |
| 2001/0008774 A1* | 7/2001 | May |
| 2003/0105299 A1 | 6/2003 | Achilefu et al. |
| 2006/0036072 A1 | 2/2006 | Licha et al. |
| 2014/0377879 A1 | 12/2014 | Sharrock et al. |
| 2015/0293086 A1 | 10/2015 | Messmer et al. |

FOREIGN PATENT DOCUMENTS

| | | |
|---|---|---|
| WO | WO 2002/077646 A1 | 10/2002 |
| WO | WO 2015/143394 A1 | 9/2015 |
| WO | WO 2017/156038 A2 | 9/2017 |

OTHER PUBLICATIONS

Ma et al., Functional screen reveals essential roles of miR-27a/24 in differentiation of embryonic stem cells, EMBO J (2015)34:361-378. (Year: 2015).*
Holtom et al., A highly sensitive and selective radioimmunoassay for the measurement of neurotensin, Journal of Neuroscience Methods 100 (2000) 151-156. (Year: 2000).*
Blast alignment, retrieved from https://blast.ncbi.nlm.nih.gov/Blast.cgi?CMD=Get&RID=8G2K1TU9114&ADV_VIEW=no&CONFIG_DESCR=2,3,4,5,6,7,8, 2pages, 2021 (Year: 2021).*
Russell et al., J. Mol. Biol. (1994) 244,332-350 (Year: 1994).*
International Search Report and Written Opinion from International Application No. PCT/US2017/021211, 16 pages, dated Aug. 25, 2017, application now published as International Publication No. WO2017/156038 on Sep. 14, 2017.
Holtom et al., "A highly sensitive and selective radioimmunoassay for the measurement of neurotensin", J. Neurosci. Meth., vol. 100, No. 1-2, pp. 151-156 (2000).

* cited by examiner

*Primary Examiner* — Changhwa J Cheu
(74) *Attorney, Agent, or Firm* — McDermott Will and Emery LLP; Judy M. Mohr; Brett A. Schweers

(57) ABSTRACT

The present invention relates to compositions and methods use in designing immunoassay controls. In various aspects, the invention provides synthetic peptides comprising the sequence CPRRPYIL or an analog thereof; ELAGLGFAELQC or an analog thereof; and CDWRKNIDAL or an analog thereof; specific binding reagents that bind to a CPRRPYIL, ELAGLGFAELQC or CDWRKNIDAL peptide; methods of producing such reagents; and assays utilizing such reagents to provide assay controls signals that are unrelated to the measurement of the analyte or analytes of interest in that no reagents used in the analyte assay(s) contribute to the control signal.

9 Claims, 1 Drawing Sheet

Specification includes a Sequence Listing.

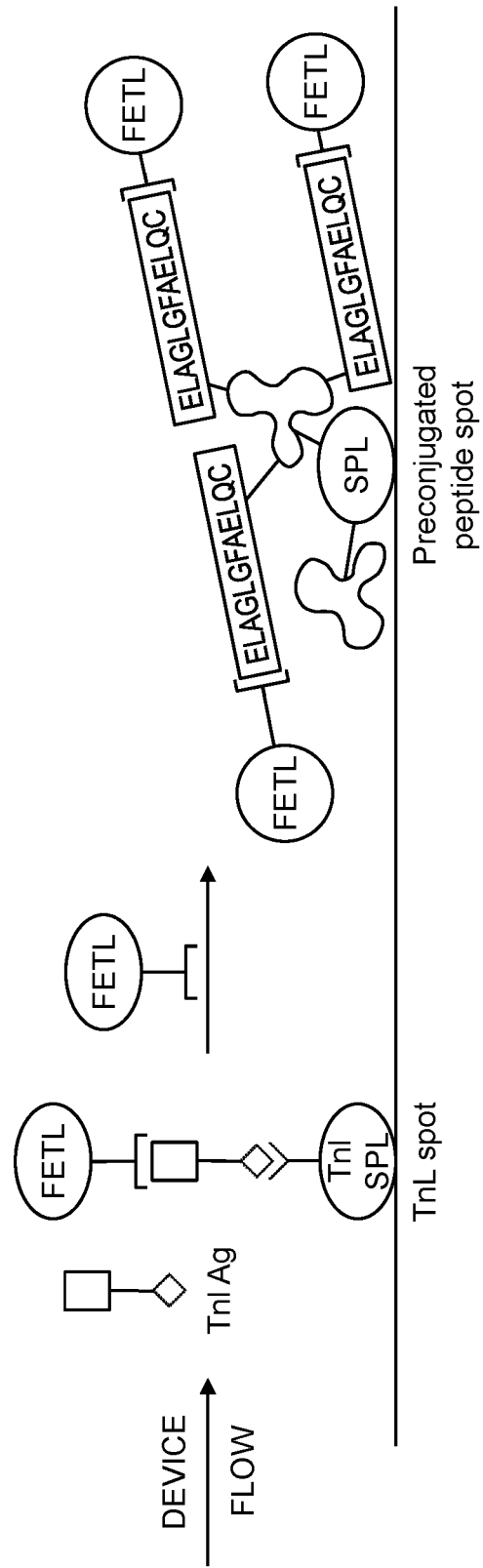

SEQUENCE LISTING

<160> NUMBER OF SEQ ID NOS: 8

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Cys Pro Arg Arg Pro Tyr Ile Leu
1               5

<210> SEQ ID NO 2
<211> LENGTH: 14
<212> TYPE: PRT
<213> ORGANISM: Artificial Sequence
<220> FEATURE:
<223> OTHER INFORMATION: Synthetic

<400> SEQUENCE: 2

Pro Leu Tyr Glu Asn Lys Pro Arg Arg Pro Tyr Ile Leu Cys
1               5                   10

<210> SEQ ID NO 3
<211> LENGTH: 170
<212> TYPE: PRT
<213> ORGANISM: Homo sapiens
<220> FEATURE:
<221> NAME/KEY: misc_feature
<223> OTHER INFORMATION: residues 156-163 of human Neurotensin

<400> SEQUENCE: 3

Met Met Ala Gly Met Lys Ile Gln Leu Val Cys Met Leu Leu Leu Ala
1               5                   10                  15

Phe Ser Ser Trp Ser Leu Cys Ser Asp Ser Glu Glu Glu Met Lys Ala
            20                  25                  30

Leu Glu Ala Asp Phe Leu Thr Asn Met His Thr Ser Lys Ile Ser Lys
        35                  40                  45

Ala His Val Pro Ser Trp Lys Met Thr Leu Leu Asn Val Cys Ser Leu
    50                  55                  60

Val Asn Asn Leu Asn Ser Pro Ala Glu Glu Thr Gly Glu Val His Glu
65                  70                  75                  80

Glu Glu Leu Val Ala Arg Arg Lys Leu Pro Thr Ala Leu Asp Gly Phe
                85                  90                  95

Ser Leu Glu Ala Met Leu Thr Ile Tyr Gln Leu His Lys Ile Cys His
            100                 105                 110

Ser Arg Ala Phe Gln His Trp Glu Leu Ile Gln Glu Asp Ile Leu Asp
        115                 120                 125

Thr Gly Asn Asp Lys Asn Gly Lys Glu Val Ile Lys Arg Lys Ile
    130                 135                 140

Pro Tyr Ile Leu Lys Arg Gln Leu Tyr Glu Asn Lys Pro Arg Arg Pro
145                 150                 155                 160

Tyr Ile Leu Lys Arg Asp Ser Tyr Tyr Tyr
                165                 170

<210> SEQ ID NO 4
<211> LENGTH: 12
<212> TYPE: PRT
<213> ORGANISM: Artificial Sequence
<220> FEATURE:
<223> OTHER INFORMATION: Synthetic

<400> SEQUENCE: 4

Glu Leu Ala Gly Leu Gly Phe Ala Glu Leu Gln Cys
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

Lys Pro Arg Arg Pro Tyr Ile Leu
1               5

<210> SEQ ID NO 6
<211> LENGTH: 12
<212> TYPE: PRT
<213> ORGANISM: Artificial Sequence
<220> FEATURE:
<223> OTHER INFORMATION: Synthetic

<400> SEQUENCE: 6

Glu Leu Ala Gly Leu Gly Phe Ala Glu Leu Gln Asp
1               5                   10

<210> SEQ ID NO 7
<211> LENGTH: 210
<212> TYPE: PRT
<213> ORGANISM: Homo sapiens
<220> FEATURE:
<221> NAME/KEY: misc_feature
<223> OTHER INFORMATION: residues 84-95 of human Troponin I from cardiac
      muscle

<400> SEQUENCE: 7

Met Ala Asp Gly Ser Ser Asp Ala Ala Arg Glu Pro Arg Pro Ala Pro
1               5                   10                  15

Ala Pro Ile Arg Arg Arg Ser Ser Asn Tyr Arg Ala Tyr Ala Thr Glu
                20                  25                  30

Pro His Ala Lys Lys Lys Ser Lys Ile Ser Ala Ser Arg Lys Leu Gln
            35                  40                  45

Leu Lys Thr Leu Leu Leu Gln Ile Ala Lys Gln Glu Leu Glu Arg Glu
    50                  55                  60

Ala Glu Glu Arg Arg Gly Glu Lys Gly Arg Ala Leu Ser Thr Arg Cys
65                  70                  75                  80

Gln Pro Leu Glu Leu Ala Gly Leu Gly Phe Ala Glu Leu Gln Asp Leu
                85                  90                  95

Cys Arg Gln Leu His Ala Arg Val Asp Lys Val Asp Glu Glu Arg Tyr
            100                 105                 110

Asp Ile Glu Ala Lys Val Thr Lys Asn Ile Thr Glu Ile Ala Asp Leu
    115                 120                 125

Thr Gln Lys Ile Phe Asp Leu Arg Gly Lys Phe Lys Arg Pro Thr Leu
130                 135                 140

Arg Arg Val Arg Ile Ser Ala Asp Ala Met Met Gln Ala Leu Leu Gly
145                 150                 155                 160

Ala Arg Ala Lys Glu Ser Leu Asp Leu Arg Ala His Leu Lys Gln Val
                165                 170                 175

Lys Lys Glu Asp Thr Glu Lys Glu Asn Arg Glu Val Gly Asp Trp Arg
            180                 185                 190

```
Lys Asn Ile Asp Ala Leu Ser Gly Met Glu Gly Arg Lys Lys Lys Phe
        195                 200                 205
Glu Ser
    210

<210> SEQ ID NO 8
<211> LENGTH: 10
<212> TYPE: PRT
<213> ORGANISM: Artificial Sequence
<220> FEATURE:
<223> OTHER INFORMATION: Synthetic

<400> SEQUENCE: 8

Cys Asp Trp Arg Lys Asn Ile Asp Ala Leu
1               5                   10
```

IMMUNOASSAY CONTROLS AND THE USE THEREOF

CROSS-REFERENCE TO RELATED APPLICATIONS

The present invention is a U.S. National Stage Application under 35 U.S.C. § 371 which claims the benefit of priority from International Patent Application No. PCT/US2017/021211, filed Mar. 7, 2017, which claims the benefit of priority from U.S. Provisional Application No. 62/304,762, filed Mar. 7, 2016, and from U.S. Provisional Application No. 62/346,347, filed Jun. 6, 2016, each of which is hereby incorporated by reference in its entirety including all tables, figures, and claims.

The present invention claims priority from U.S. Provisional Application No. 62/304,762, filed Mar. 7, 2016, and from U.S. Provisional Application No. 62/346,347, filed Jun. 6, 2016, each of which is hereby incorporated in its entirety including all tables, figures, and claims.

FIELD OF THE INVENTION

The present invention relates to methods and compositions for measuring the amount of an analyte using assays, particularly immunoassays and, in certain embodiments, immunochromatographic assays.

BACKGROUND OF THE INVENTION

The following discussion of the background of the invention is merely provided to aid the reader in understanding the invention and is not admitted to describe or constitute prior art to the present invention.

Due to their simplicity, relative accuracy, fast result reporting, and user-friendliness, specific binding assays, and in particular immunoassays, have undergone tremendous growth in the diagnostic industry. Such technology has been utilized widely for pregnancy and woman's health determination, cardiac and emergency conditions monitoring and testing, infectious disease including, virus screening, cancer marker screening, and drugs of abuse testing. However, as with any laboratory technique, each observation in such an assay is not only a function of the analyte of interest, but also a function of multiple sources of variation which convolute the result. These sources of variation stem from both biological and technical factors. Biological factors include the properties of the sample matrix, the characteristics of individual patients, and the characteristics of the biological molecules (e.g., antibodies) used in the test. Technical factors, such as device variations, temperature, degradation of the test system with time, etc., combine with the biological factors involved to affect the precision, sensitivity, reproducibility, and specificity of the assay. In the case of lateral flow assays, the flow of fluid through the lateral flow membrane, as well as the viscosity of the fluid sample and other factors, can contribute to limitations on performance of the assays.

Strategies exist for mitigating the impact of these convoluting factors. For example, blocking strategies are employed to prevent the confounding effects of non-specific binding. Additionally, normalization of the data is performed to remove unwanted systematic variance introduced by technical factors. U.S. Pat. Nos. 5,356,782, 5,753,517, 7,691,595, and 7,713,703 describe various assay platforms comprising assay controls which attempt to deconvolute immunoassay data. By deconvoluting the biological and technical effects from the data, a more accurate test result may be obtained.

BRIEF SUMMARY OF THE INVENTION

It is an object of the invention to provide compositions and methods use in designing immunoassay controls.

In various aspects, the invention provides synthetic peptides comprising the sequence CPRRPYIL (SEQ ID NO: 1) or an analog thereof (referred to defined below as "a CPRRPYIL (SEQ ID NO: 1) peptide"); specific binding reagents that bind to a CPRRPYIL (SEQ ID NO: 1) peptide; methods of producing such reagents; and assays utilizing such reagents to provide assay controls signals that are unrelated to the measurement of the analyte or analytes of interest in that no reagents used in the analyte assay(s) contribute to the control signal. In certain aspects, the binding of the specific binding reagent to the CPRRPYIL (SEQ ID NO: 1) peptide is used to normalize or otherwise modulate an assay result.

In various aspects, the invention also provides synthetic peptides comprising the sequence ELAGLGFAELQC (SEQ ID NO: 4) or an analog thereof (referred to defined below as "a ELAGLGFAELQC (SEQ ID NO: 4) peptide"); specific binding reagents that bind to a ELAGLGFAELQC (SEQ ID NO: 4) peptide; methods of producing such reagents; and assays utilizing such reagents to provide assay controls signals that are unrelated to the measurement of the analyte or analytes of interest in that no reagents used in the analyte assay(s) contribute to the control signal. In certain aspects, the binding of the specific binding reagent to the ELAGLGFAELQC (SEQ ID NO: 4) peptide is used to normalize or otherwise modulate an assay result.

In various aspects, the invention also provides synthetic peptides comprising the sequence CDWRKNIDAL (SEQ ID NO: 8) or an analog thereof (referred to defined below as "a CDWRKNIDAL (SEQ ID NO: 8) peptide"); specific binding reagents that bind to a CDWRKNIDAL (SEQ ID NO: 8) peptide; methods of producing such reagents; and assays utilizing such reagents to provide assay controls signals that are unrelated to the measurement of the analyte or analytes of interest in that no reagents used in the analyte assay(s) contribute to the control signal. In certain aspects, the binding of the specific binding reagent to the CDWRKNIDAL (SEQ ID NO: 8) peptide is used to normalize or otherwise modulate an assay result.

In a first aspect, the present invention provides:
(a) a synthetic peptide comprising SEQ ID NO: 1;
(b) a synthetic peptide comprising a sequence at least 87.5% homologous to SEQ ID NO: 1 over 8 contiguous residues;
(c) a specific binding reagent (e.g., an antibody) that specifically binds a synthetic peptide of (a) and/or (b)
(d) a solid phase comprising a synthetic peptide of (a) and/or (b) immobilized on a surface thereof; and
(e) a solid phase comprising a specific binding reagent of (c) immobilized on a surface thereof;
(f) a detectable label conjugated to a synthetic peptide of (a) and/or (b); and/or
(g) a detectable label conjugated to a specific binding reagent of (c).

In a related aspect, the present invention provides an assay device for detection of at least one analyte in a sample, comprising:

a substrate defining at least one diagnostic lane;
a sample application zone on the substrate for receiving a sample;
a dried reagent zone on the substrate fluidly connected to the sample application zone;
a detection zone on the substrate comprising at least one control zone and at least one assay zone, the detection zone fluidly connected to the sample application zone and the sample application zone such that sample applied to the sample application zone flows through the dried reagent zone prior to reaching the detection zone;
wherein the at least one control zone comprises a specific binding reagent (e.g., an antibody) having binding specificity for a CPRRPYIL (SEQ ID NO: 1) peptide, and wherein the dried reagent zone comprises a CPRRPYIL (SEQ ID NO: 1) peptide, or
wherein the at least one control zone comprises a CPRRPYIL (SEQ ID NO: 1) peptide and wherein the dried reagent zone comprises a specific binding reagent (e.g., an antibody) having binding specificity for a CPRRPYIL (SEQ ID NO: 1) peptide.

In various embodiments,
(i) the control zone or dried reagent zone comprises an antibody that specifically binds a synthetic peptide comprising the sequence CPRRPYIL (SEQ ID NO: 1) (CysProArgArgProTyrIleLeu; SEQ ID NO: 1);
(ii) the dried reagent zone or the control zone comprises a synthetic peptide comprising the sequence CPRRPYIL (SEQ ID NO: 1) (CysProArgArgProTyrIleLeu; SEQ ID NO: 1);
(iii) the synthetic peptide is CPRRPYIL (SEQ ID NO: 1);
(iv) the specific binding reagent is selected from the group consisting of a monoclonal antibody, a polyclonal antibody, a Fab fragment, a Fab2 fragment, a Fv fragment, a ScFv fragment, or other peptide fragment thereof that to specifically binds SEQ ID NO: 1;
(v) the CPRRPYIL (SEQ ID NO: 1) peptide is conjugated to, or bound by a peptide bond to, an epitope sequence comprising an epitope of Cardiac troponin I, an epitope of brain natriuretic peptide, an epitope of placental growth factor, an epitope of soluble fms like tyrosine, and/or an epitope of endoglin.
(vi) the CPRRPYIL (SEQ ID NO: 1) peptide has been combined with a detectable label, wherein the detectable label is preferably an enzyme, a metal sol particle, a latex particle, a magnetically susceptible particle, and most preferably a fluorescently labelled latex particle; and/or
(vii) the dried reagent zone or the control zone comprises an antibody that has been combined with a detectable label, wherein the detectable label is preferably an enzyme, a metal sol particle, a latex particle, a magnetically susceptible particle, and most preferably a fluorescently labelled latex particle.

In another aspect, the present invention provides a method of normalising an assay result for a specific binding (e.g., an immunoassay), comprising;
providing an assay device as described herein;
applying a sample to the sample application zone;
forming a mixture within the reagent zone between the sample and a reagent incorporated in the reagent zone;
flowing the sample reagent mixture along the diagnostic lane;
detecting a response due to interaction of a component of the sample reagent mixture at the control zone;
detecting a response due to interaction of a component of the sample reagent mixture at the assay zone; and
modulating the response at the assay zone based on the response obtained at the control zone.

In various embodiments of the method,
(i) a response at the control zone occurs uniquely as a result of reagents incorporated in the reagent zone;
(ii) a response at the control zone does not occur due to components of the sample; and/or
(iii) the response at the assay zone is either increased or decreased based on the response at the control zone.

In yet another aspect, the present invention provides a device comprising;
a substrate defining at least one diagnostic lane;
a sample application zone;
a dried reagent zone;
a detection zone comprising a combined assay and control zone;
wherein the combined assay and control zone comprises a first specific binding reagent (e.g., an antibody) having binding specificity for a CPRRPYIL (SEQ ID NO: 1) peptide and a second specific binding reagent specific for an analyte of interest.

In various embodiments, the device is further defined as follows:
(i) the first specific binding reagent is an antibody that specifically binds a peptide comprising the sequence of SEQ ID NO: 1, wherein the peptide is preferably CPRRPYIL (SEQ ID NO: 1);
(ii) the dried reagent zone or the combined assay and control zone comprises a peptide comprising the sequence of SEQ ID NO: 1, wherein the peptide is preferably CPRRPYIL (SEQ ID NO: 1);
(iii) the specific binding reagent is selected from the group consisting of a monoclonal antibody, a polyclonal antibody, a Fab fragment, a Fab2 fragment, a Fv fragment, a ScFv fragment, or other peptide fragment thereof that to specifically binds SEQ ID NO: 1;
(iv) the dried reagent zone or the combined assay and control zone comprises a peptide that has been combined with a detectable label, wherein the detectable label is preferably an enzyme, a metal sol particle, a latex particle, a magnetically susceptible particle, and most preferably a fluorescently labelled latex particle;
(v) the dried reagent zone or the control zone comprises an antibody that has been combined with a detectable label, wherein the detectable label is preferably an enzyme, a metal sol particle, a latex particle, a magnetically susceptible particle, and most preferably a fluorescently labelled latex particle.

In another aspect, the present invention provides a method of normalising an assay result for a specific binding (e.g., an immunoassay), comprising;
providing a device as described herein, wherein the CPRRPYIL (SEQ ID NO: 1) peptide is conjugated to, or bound by a peptide bond to, an epitope sequence comprising an epitope of Cardiac troponin I, an epitope of brain natriuretic peptide, an epitope of placental growth factor, an epitope of soluble fms like tyrosine, and/or an epitope of endoglin;
applying a sample to the sample application zone;
forming a mixture within the reagent zone between the sample, the fluorescent labelled particle and the CPRRPYIL (SEQ ID NO: 1) peptide, whereby both target analyte and the CPRRPYIL (SEQ ID NO: 1) peptide are bound by specific binding reagent on the fluorescent labelled particle;
flowing the sample reagent mixture along the diagnostic lane;

detecting a response due to interaction of the epitope of SEQ ID NO: 1 present on the CPRRPYIL (SEQ ID NO: 1) peptide with an antibody immobilised at the control zone;

detecting a response due to interaction of an epitope of the target analyte with an antibody immobilised at the assay zone; and modulating the response at the assay zone based on the response obtained at the control zone.

In various embodiments of the method, (i) a response at the control zone occurs uniquely as a result of the CPRRPYIL (SEQ ID NO: 1) peptide;

(ii) a response at the control zone does not occur due to components of the sample;

(iii) the response determined at the assay zone is either increased or decreased based on the response at the control zone; and (iv) the CPRRPYIL (SEQ ID NO: 1) peptide consists of CPRRPYIL (SEQ ID NO: 1) and a peptide sequence unique to the target analyte.

In another aspect, the present invention provides:

(a) a synthetic peptide comprising SEQ ID NO: 4;

(b) a synthetic peptide comprising a sequence at least 87.5% homologous to SEQ ID NO: 4 over 8 contiguous residues;

(c) a specific binding reagent (e.g., an antibody) that specifically binds a synthetic peptide of (a) and/or (b)

(d) a solid phase comprising a synthetic peptide of (a) and/or (b) immobilized on a surface thereof; and (e) a solid phase comprising a specific binding reagent of (c) immobilized on a surface thereof;

(f) a detectable label conjugated to a synthetic peptide of (a) and/or (b); and/or (g) a detectable label conjugated to a specific binding reagent of (c).

In a related aspect, the present invention provides an assay device for detection of at least one analyte in a sample, comprising:

a substrate defining at least one diagnostic lane;

a sample application zone on the substrate for receiving a sample;

a dried reagent zone on the substrate fluidly connected to the sample application zone;

a detection zone on the substrate comprising at least one control zone and at least one assay zone, the detection zone fluidly connected to the sample application zone and the sample application zone such that sample applied to the sample application zone flows through the dried reagent zone prior to reaching the detection zone;

wherein the at least one control zone comprises a specific binding reagent (e.g., an antibody) having binding specificity for a ELAGLGFAELQC (SEQ ID NO: 4) peptide, and wherein the dried reagent zone comprises a ELAGLGFAELQC (SEQ ID NO: 4) peptide, or wherein the at least one control zone comprises a ELAGLGFAELQC (SEQ ID NO: 4) peptide and wherein the dried reagent zone comprises a specific binding reagent (e.g., an antibody) having binding specificity for a ELAGLGFAELQC (SEQ ID NO: 4) peptide.

In various embodiments, (i) the control zone or dried reagent zone comprises an antibody that specifically binds a synthetic peptide comprising the sequence ELAGLGFAELQC (SEQ ID NO: 4);

(ii) the dried reagent zone or the control zone comprises a synthetic peptide comprising the sequence ELAGLGFAELQC (SEQ ID NO: 4);

(iii) the synthetic peptide is ELAGLGFAELQC (SEQ ID NO: 4);

(iv) the specific binding reagent is selected from the group consisting of a monoclonal antibody, a polyclonal antibody, a Fab fragment, a Fab2 fragment, a Fv fragment, a ScFv fragment, or other peptide fragment thereof that to specifically binds SEQ ID NO: 4;

(v) the ELAGLGFAELQC (SEQ ID NO: 4) peptide is conjugated to, or bound by a peptide bond to, an epitope sequence comprising an epitope of Cardiac troponin I, an epitope of brain natriuretic peptide, an epitope of placental growth factor, an epitope of soluble fms like tyrosine, and/or an epitope of endoglin.

(vi) the ELAGLGFAELQC (SEQ ID NO: 4) peptide has been combined with a detectable label, wherein the detectable label is preferably an enzyme, a metal sol particle, a latex particle, a magnetically susceptible particle, and most preferably a fluorescently labelled latex particle; and/or (vii) the dried reagent zone or the control zone comprises an antibody that has been combined with a detectable label, wherein the detectable label is preferably an enzyme, a metal sol particle, a latex particle, a magnetically susceptible particle, and most preferably a fluorescently labelled latex particle.

In another aspect, the present invention provides a method of normalising an assay result for a specific binding (e.g., an immunoassay), comprising;

providing an assay device as described herein;

applying a sample to the sample application zone;

forming a mixture within the reagent zone between the sample and a reagent incorporated in the reagent zone;

flowing the sample reagent mixture along the diagnostic lane:

detecting a response due to interaction of a component of the sample reagent mixture at the control zone;

detecting a response due to interaction of a component of the sample reagent mixture at the assay zone; and modulating the response at the assay zone based on the response obtained at the control zone.

In various embodiments of the method, (i) a response at the control zone occurs uniquely as a result of reagents incorporated in the reagent zone;

(ii) a response at the control zone does not occur due to components of the sample; and/or (iii) the response at the assay zone is either increased or decreased based on the response at the control zone.

In yet another aspect, the present invention provides a device comprising;

a substrate defining at least one diagnostic lane;

a sample application zone;

a dried reagent zone;

a detection zone comprising a combined assay and control zone;

wherein the combined assay and control zone comprises a first specific binding reagent (e.g., an antibody) having binding specificity for a ELAGLGFAELQC (SEQ ID NO: 4) peptide and a second specific binding reagent specific for an analyte of interest.

In various embodiments, the device is further defined as follows:

(i) the first specific binding reagent is an antibody that specifically binds a peptide comprising the sequence of SEQ ID NO: 4, wherein the peptide is preferably ELAGLGFAELQC (SEQ ID NO: 4);

(ii) the dried reagent zone or the combined assay and control zone comprises a peptide comprising the sequence of SEQ ID NO: 4, wherein the peptide is preferably ELAGLGFAELQC (SEQ ID NO: 4);

(iii) the specific binding reagent is selected from the group consisting of a monoclonal antibody, a polyclonal antibody, a Fab fragment, a Fab2 fragment, a Fv fragment, a ScFv fragment, or other peptide fragment thereof that to specifically binds SEQ ID NO: 4;

(iv) the dried reagent zone or the combined assay and control zone comprises a peptide that has been combined with a detectable label, wherein the detectable label is preferably an enzyme, a metal sol particle, a latex particle, a magnetically susceptible particle, and most preferably a fluorescently labelled latex particle;

(v) the dried reagent zone or the control zone comprises an antibody that has been combined with a detectable label, wherein the detectable label is preferably an enzyme, a metal sol particle, a latex particle, a magnetically susceptible particle, and most preferably a fluorescently labelled latex particle In another aspect, the present invention provides a method of normalising an assay result for a specific binding (e.g., an immunoassay), comprising;
  providing a device as described herein, wherein the ELAGLGFAELQC (SEQ ID NO: 4) peptide is conjugated to, or bound by a peptide bond to, an epitope sequence comprising an epitope of Cardiac troponin I, an epitope of brain natriuretic peptide, an epitope of placental growth factor, an epitope of soluble fms like tyrosine, and/or an epitope of endoglin;
  applying a sample to the sample application zone;
  forming a mixture within the reagent zone between the sample, the fluorescent labelled particle and the ELAGLGFAELQC (SEQ ID NO: 4) peptide, whereby both target analyte and the ELAGLGFAELQC (SEQ ID NO: 4) peptide are bound by specific binding reagent on the fluorescent labelled particle;
  flowing the sample reagent mixture along the diagnostic lane:
  detecting a response due to interaction of the epitope of SEQ ID NO: 4 present on the ELAGLGFAELQC (SEQ ID NO: 4) peptide with an antibody immobilised at the control zone;
  detecting a response due to interaction of an epitope of the target analyte with an antibody immobilised at the assay zone; and
  modulating the response at the assay zone based on the response obtained at the control zone.

In various embodiments of the method,
(i) a response at the control zone occurs uniquely as a result of the ELAGLGFAELQC (SEQ ID NO: 4) peptide;
(ii) a response at the control zone does not occur due to components of the sample;
(iii) the response determined at the assay zone is either increased or decreased based on the response at the control zone; and
(iv) the ELAGLGFAELQC (SEQ ID NO: 4) peptide consists of ELAGLGFAELQC (SEQ ID NO: 4) and a peptide sequence unique to the target analyte.

In another aspect, the present invention provides:
  (a) a synthetic peptide comprising SEQ ID NO: 8;
  (b) a synthetic peptide comprising a sequence at least 87.5% homologous to SEQ ID NO: 8 over 8 contiguous residues;
  (c) a specific binding reagent (e.g., an antibody) that specifically binds a synthetic peptide of (a) and/or (b)
  (d) a solid phase comprising a synthetic peptide of (a) and/or (b) immobilized on a surface thereof; and
  (e) a solid phase comprising a specific binding reagent of (c) immobilized on a surface thereof;
  (f) a detectable label conjugated to a synthetic peptide of (a) and/or (b); and/or
  (g) a detectable label conjugated to a specific binding reagent of (c).

In a related aspect, the present invention provides an assay device for detection of at least one analyte in a sample, comprising:
  a substrate defining at least one diagnostic lane;
  a sample application zone on the substrate for receiving a sample;
  a dried reagent zone on the substrate fluidly connected to the sample application zone;
  a detection zone on the substrate comprising at least one control zone and at least one assay zone, the detection zone fluidly connected to the sample application zone and the sample application zone such that sample applied to the sample application zone flows through the dried reagent zone prior to reaching the detection zone;
  wherein the at least one control zone comprises a specific binding reagent (e.g., an antibody) having binding specificity for a CDWRKNIDAL (SEQ ID NO: 8) peptide, and wherein the dried reagent zone comprises a CDWRKNIDAL (SEQ ID NO: 8) peptide, or
  wherein the at least one control zone comprises a CDWRKNIDAL (SEQ ID NO: 8) peptide and wherein the dried reagent zone comprises a specific binding reagent (e.g., an antibody) having binding specificity for a CDWRKNIDAL (SEQ ID NO: 8) peptide.

In various embodiments,
(i) the control zone or dried reagent zone comprises an antibody that specifically binds a synthetic peptide comprising the sequence CDWRKNIDAL (SEQ ID NO: 8);
(ii) the dried reagent zone or the control zone comprises a synthetic peptide comprising the sequence CDWRKNIDAL (SEQ ID NO: 8);
(iii) the synthetic peptide is CDWRKNIDAL (SEQ ID NO: 8);
(iv) the specific binding reagent is selected from the group consisting of a monoclonal antibody, a polyclonal antibody, a Fab fragment, a Fab2 fragment, a Fv fragment, a ScFv fragment, or other peptide fragment thereof that to specifically binds SEQ ID NO: 8;
(v) the CDWRKNIDAL (SEQ ID NO: 8) peptide is conjugated to, or bound by a peptide bond to, an epitope sequence comprising an epitope of Cardiac troponin I, an epitope of brain natriuretic peptide, an epitope of placental growth factor, an epitope of soluble fms like tyrosine, and/or an epitope of endoglin.
(vi) the CDWRKNIDAL (SEQ ID NO: 8) peptide has been combined with a detectable label, wherein the detectable label is preferably an enzyme, a metal sol particle, a latex particle, a magnetically susceptible particle, and most preferably a fluorescently labelled latex particle; and/or
(vii) the dried reagent zone or the control zone comprises an antibody that has been combined with a detectable label, wherein the detectable label is preferably an enzyme, a metal sol particle, a latex particle, a magnetically susceptible particle, and most preferably a fluorescently labelled latex particle.

In another aspect, the present invention provides a method of normalising an assay result for a specific binding (e.g., an immunoassay), comprising;

providing an assay device as described herein;
applying a sample to the sample application zone;
forming a mixture within the reagent zone between the sample and a reagent incorporated in the reagent zone;
flowing the sample reagent mixture along the diagnostic lane:
detecting a response due to interaction of a component of the sample reagent mixture at the control zone;
detecting a response due to interaction of a component of the sample reagent mixture at the assay zone; and
modulating the response at the assay zone based on the response obtained at the control zone.

In various embodiments of the method,
(i) a response at the control zone occurs uniquely as a result of reagents incorporated in the reagent zone;
(ii) a response at the control zone does not occur due to components of the sample; and/or
(iii) the response at the assay zone is either increased or decreased based on the response at the control zone.

In yet another aspect, the present invention provides a device comprising;
a substrate defining at least one diagnostic lane;
a sample application zone;
a dried reagent zone;
a detection zone comprising a combined assay and control zone;
wherein the combined assay and control zone comprises a first specific binding reagent (e.g., an antibody) having binding specificity for a CDWRKNIDAL (SEQ ID NO: 8) peptide and a second specific binding reagent specific for an analyte of interest.

In various embodiments, the device is further defined as follows:
(i) the first specific binding reagent is an antibody that specifically binds a peptide comprising the sequence of SEQ ID NO: 8, wherein the peptide is preferably CDWRKNIDAL (SEQ ID NO: 8);
(ii) the dried reagent zone or the combined assay and control zone comprises a peptide comprising the sequence of SEQ ID NO: 8, wherein the peptide is preferably CDWRKNIDAL (SEQ ID NO: 8);
(iii) the specific binding reagent is selected from the group consisting of a monoclonal antibody, a polyclonal antibody, a Fab fragment, a Fab2 fragment, a Fv fragment, a ScFv fragment, or other peptide fragment thereof that to specifically binds SEQ ID NO: 8;
(iv) the dried reagent zone or the combined assay and control zone comprises a peptide that has been combined with a detectable label, wherein the detectable label is preferably an enzyme, a metal sol particle, a latex particle, a magnetically susceptible particle, and most preferably a fluorescently labelled latex particle;
(v) the dried reagent zone or the control zone comprises an antibody that has been combined with a detectable label, wherein the detectable label is preferably an enzyme, a metal sol particle, a latex particle, a magnetically susceptible particle, and most preferably a fluorescently labelled latex particle In another aspect, the present invention provides a method of normalising an assay result for a specific binding (e.g., an immunoassay), comprising;
providing a device as described herein, wherein the CDWRKNIDAL (SEQ ID NO: 8) peptide is conjugated to, or bound by a peptide bond to, an epitope sequence comprising an epitope of Cardiac troponin I, an epitope of brain natriuretic peptide, an epitope of placental growth factor, an epitope of soluble fms like tyrosine, and/or an epitope of endoglin;
applying a sample to the sample application zone;
forming a mixture within the reagent zone between the sample, the fluorescent labelled particle and the CDWRKNIDAL (SEQ ID NO: 8) peptide, whereby both target analyte and the CDWRKNIDAL (SEQ ID NO: 8) peptide are bound by specific binding reagent on the fluorescent labelled particle;
flowing the sample reagent mixture along the diagnostic lane:
detecting a response due to interaction of the epitope of SEQ ID NO: 8 present on the CDWRKNIDAL (SEQ ID NO: 8) peptide with an antibody immobilised at the control zone;
detecting a response due to interaction of an epitope of the target analyte with an antibody immobilised at the assay zone; and
modulating the response at the assay zone based on the response obtained at the control zone.

In various embodiments of the method,
(i) a response at the control zone occurs uniquely as a result of the CDWRKNIDAL (SEQ ID NO: 8) peptide;
(ii) a response at the control zone does not occur due to components of the sample;
(iii) the response determined at the assay zone is either increased or decreased based on the response at the control zone; and
(iv) the CDWRKNIDAL (SEQ ID NO: 8) peptide consists of CDWRKNIDAL (SEQ ID NO: 8) and a peptide sequence unique to the target analyte.

The skilled artisan will recognize that the CPRRPYIL (SEQ ID NO: 1) peptide and its corresponding antibody described herein, the ELAGLGFAELQC (SEQ ID NO: 4) peptide and its corresponding antibody described herein, and the CDWRKNIDAL (SEQ ID NO: 8) peptide and its corresponding antibody described herein may also be used together within the same device. Thus, in certain aspects, the invention provides a device comprising;
a substrate defining at least one diagnostic lane;
a sample application zone;
a dried reagent zone; and
a detection zone comprising at least one control zone and at least one assay zone;
wherein one or more of a-f are true:
(a) the at least one control zone comprises an antibody that specifically binds a peptide having a sequence at least 87.5% homologous to SEQ ID NO: 1, and wherein the dried reagent zone comprises a peptide having 87.5% homology to SEQ ID NO: 1, or
(b) the at least one control zone comprises a peptide having 87.5% homology to SEQ ID NO: 1 and wherein the dried reagent zone comprises an antibody that specifically binds a peptide having a sequence at least 87.5% homologous to SEQ ID NO: 1, or
(c) the at least one control zone comprises an antibody that specifically binds a peptide having a sequence at least 87.5% homologous to SEQ ID NO: 4, and wherein the dried reagent zone comprises a peptide having 87.5% homology to SEQ ID NO: 4, or
(d) the at least one control zone comprises a peptide having 87.5% homology to SEQ ID NO: 4 and wherein the dried reagent zone comprises an antibody that specifically binds a peptide having a sequence at least 87.5% homologous to SEQ ID NO: 4, or
(e) the at least one control zone comprises an antibody that specifically binds a peptide having a sequence at least 87.5% homologous to SEQ ID NO: 8, and wherein the dried reagent zone comprises a peptide having 87.5% homology to SEQ ID NO: 8, or
(f) the at least one control zone comprises a peptide having 87.5% homology to SEQ ID NO: 8 and wherein the dried reagent zone comprises an antibody that specifically binds a peptide having a sequence at least 87.5% homologous to SEQ ID NO: 8.

In certain embodiments, at least one of (a) and (b) are true, at least one of (c) and (d) are true, and at least one of (e) and (f) are true.

In certain embodiments, the antibody that specifically binds a peptide having a sequence at least 87.5% homologous to SEQ ID NO: 1 is an antibody that specifically binds a peptide having the sequence CPRRPYIL (SEQ ID NO: 1), and preferably the peptide having a sequence at least 87.5% homologous to SEQ ID NO: 1 is a peptide comprising SEQ ID NO: 1. Most preferably, the peptide consists of SEQ ID NO: 1.

In certain embodiments, the antibody that specifically binds a peptide having a sequence at least 87.5% homologous to SEQ ID NO: 4 is an antibody that specifically binds a peptide having the sequence ELAGLGFAELQC (SEQ ID NO: 4), and preferably the peptide having a sequence at least 87.5% homologous to SEQ ID NO: 4 is a peptide comprising SEQ ID NO: 4. Most preferably, the peptide consists of SEQ ID NO: 4.

In certain embodiments, the antibody that specifically binds a peptide having a sequence at least 87.5% homologous to SEQ ID NO: 8 is an antibody that specifically binds a peptide having the sequence CDWRKNIDAL (SEQ ID NO: 8), and preferably the peptide having a sequence at least 87.5% homologous to SEQ ID NO: 8 is a peptide comprising SEQ ID NO: 8. Most preferably, the peptide consists of SEQ ID NO: 8.

The dried reagent zone or the control zone can include a peptide or an antibody that has been combined with a detectable label. The detectable label may be an enzyme, a metal sol particle, a latex particle, a magnetically susceptible particle, or a fluorescently labelled latex particle. Other embodiments of the invention will be apparent from the following detailed description, exemplary embodiments, and claims.

BRIEF DESCRIPTION OF THE FIGURES

FIG. 1 depicts an exemplary assay device of the invention.

DETAILED DESCRIPTION OF THE INVENTION

The present invention relates to methods and compositions for measuring the amount of an analyte using assays, particularly immunoassays, and in certain embodiments immunochromatographic assays. In particular, the invention relates to assays in which controls are provided which utilize specific binding reagents unrelated to the measurement of the analyte or analytes of interest. These specific binding reagents bind to a peptide having the sequence CPRRPYIL (SEQ ID NO: 1) or an analog thereof (referred to collectively herein as "a CPRRPYIL peptide"); to a peptide having the sequence ELAGLGFAELQC (SEQ ID NO: 4) or an analog thereof (referred to collectively herein as "a ELAGLGFAELQC peptide"); or to a peptide having the sequence CDWRKNIDAL (SEQ ID NO: 8) or an analog thereof (referred to collectively herein as "a CDWRKNIDAL peptide"). As described hereinafter, the binding of the specific binding reagent to the CPRRPYIL, ELAGLGFAELQC, or CDWRKNIDAL peptide is used to normalize or otherwise modulate an assay result.

For the sake of clarity, definitions for the following terms regarding the compounds of the present invention are provided.

An "assay," as used herein, refers to an in vitro procedure for analysis of a sample to determine the presence, absence, or quantity of one or more analytes. The assays of the inventions typically utilize an analyte and at least one analyte binding agent which specifically binds to the analyte. The analyte and the analyte binding agent are members of a specific "binding pair," in which a first member of the binding pair (e.g., analyte) reacts specifically with a second member (e.g., the binding agent). One or both members of the binding pair can be an antibody. For example, a first member of the binding pair (e.g., an analyte of interest) can be an antibody, and a second member of the binding pair (e.g., a binding agent) can be anti-immunoglobulin antibody; alternatively, the first member of the binding pair (e.g., the analyte) can be an antigen, and the second member of the binding pair (e.g., the binding agent) can be an antibody (referred to herein as "an immunoassay").

In a preferred embodiment, the assay is a "sandwich" assay, which is a test for an analyte in which a fluid sample to be assessed for the presence or absence, or quantity of analyte, is contacted a first analyte binding agent, such as an antibody, which binds to the analyte, and a second analyte binding reagent which also binds to the analyte. The "sandwich" complex of the analyte and the two binding reagents is detected. Typically in this format, one antibody is detectably labeled, and the other antibody is bound to a solid phase.

The term "lateral flow assay" refers to an assay format in which a sample is applied to a lateral flow matrix. The sample flows along the lateral flow matrix, and one or more analyte components to be detected in the sample react with at least one reagent which is provided in or added to the lateral flow matrix. At least one reagent is typically immobilized in the device for reaction with the analyte component to be detected or a reagent thereof, and labels are typically employed to measure the extent of reaction with an immobilized reagent. See, e.g., U.S. patents and patent application publications: U.S. Pat. Nos. 5,602,040; 5,622,871; 5,656,503; 6,187,598; 6,228,660; 6,818,455; 2001/0008774; 2005/0244986; 6,352,862; 2003/0207465; 2003/0143755; 2003/0219908; U.S. Pat. Nos. 5,714,389; 5,989,921; 6,485,982; 11/035,047; 5,656,448; 5,559,041; 5,252,496; 5,728,587; 6,027,943; 6,506,612; 6,541,277; 6,737,277 B1; 5,073,484; 5,654,162; 6,020,147; 4,956,302; 5,120,643; 6,534,320; 4,942,522; 4,703,017; 4,743,560; 5,591,645; and RE 38,430. Lateral flow assay devices may comprise a housing having a sample port and a result window downstream of the sample port, and, optionally, a control window downstream of the result window. The sample port is adapted to receive a quantity of liquid buffer or sample applied thereto which traverses a lateral flow path via a lateral flow matrix within the housing, extending from the sample port to a downstream location. The housing may be formed of any suitable material, an example of which comprises molded plastic, and is preferably sufficiently rigid to provide support and stability for the lateral flow path or paths housed therein adhesive may be is assembled on a housing surface with the adhesive facing the lateral flow matrix to assist in maintaining the lateral flow matrix in position within the housing.

In certain embodiments of the assays of the invention, one or more of the binding agents are not antibodies: for example, the first member of the binding pair can be a ligand, and the second member of the binding pair can be a receptor; alternatively, the first member of the binding pair can be a lectin, and the second member of the binding pair can be a sugar. In still another embodiment, the first member of the binding pair can be a nucleic acid (e.g., DNA, RNA), and the second member of the binding pair can be a nucleic acid which specifically hybridizes to the first member of the binding pair. Regardless of the composition of the analyte and the binding agent, these two components nevertheless form a specific binding pair, in which the first member reacts specifically with the second member. Specific interaction between the members of the binding pair indicates that the first member of the binding pair preferentially binds or otherwise interacts with the second member of the binding pair, preferably to the exclusion of any binding to another compound in the assay.

The terms, "analyte" or "analyte of interest," as used herein, refer to a molecule or compound for which the amount will be measured. Examples of analytes include spores; proteins, such as hormones or enzymes; glycoproteins; peptides; small molecules; polysaccharides; antibodies; nucleic acids; drugs; toxins (e.g., environmental toxins); viruses or virus particles; portions of a cell wall; and other compounds. In a preferred embodiment, the analyte is "immunogenic," which indicates that antibodies (as described below) can be raised to the analyte, or to an analyte that is bound to a carrier (e.g., a hapten-carrier conjugate, for which antibodies can be raised to the hapten). In some representative embodiments, the analyte of interest can be myoglobin; CK-MB; troponin I; PSA; digoxin; theophylline; a hormone (e.g., T-3 or T-4); a drug of abuse (LSD, THC, barbituates, etc.); or a spore of Bacillus anthracis (anthrax). The analyte of interest can be in a liquid sample; alternatively, the analyte of interest can be in a dry (non-fluid) sample (e.g., a solid, such as a particulate sample, powder sample, or soil sample).

In the certain embodiments, a fluid sample is assessed for the presence or absence, or quantity, of an analyte of interest. The fluid can be a fluid that wets the membrane material; that supports a reaction between the analyte of interest and the analyte binding agent, such as the antibody/antigen reaction (i.e., does not interfere with antibody/antigen interaction); and that has a viscosity that is sufficiently low to allow movement of the fluid by capillary action. In a preferred embodiment, the fluid is an aqueous solution (such as a bodily fluid). The fluid sample can be a fluid having relatively few components, for example, an aqueous solution containing the analyte of interest; alternatively, the fluid sample can be a fluid having many components, such as a complex environmental sample (e.g., sewage, waste water, groundwater, or other water sample), or a complex biological fluid (e.g., whole blood, plasma, serum, urine, cerebrospinal fluid, saliva, semen, vitreous fluid, synovial fluid, or other biological fluid). In a preferred embodiment in which the fluid is a biological fluid, the fluid is whole blood, plasma, or serum. If desired, the fluid sample can be diluted; for example, if a complex biological fluid is used as the fluid sample, it can be diluted with a solution (e.g., an aqueous solution).

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3$^{rd}$ Edition, W. E. Paul, ed., Raven Press, N.Y. (1993); Wilson (1994) J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

The term "polypeptide" as used herein refers to a molecule having a sequence of amino acids linked by peptide bonds. This term includes proteins, fusion proteins, oligopeptides, cyclic peptides, and polypeptide derivatives. Antibodies and antibody derivatives are discussed above in a separate section, but antibodies and antibody derivatives are, for purposes of the invention, treated as a subclass of the polypeptides and derivatives. The term protein refers to a polypeptide that is isolated from a natural source, or produced from an isolated cDNA using recombinant DNA technology, and that has a sequence of amino acids having a length of at least about 200 amino acids.

The term "peptide" as used herein refers to a polypeptide of 70 amino acids or less, more preferably 50 amino acids or less, and still more preferably 25 amino acids or less, and most preferably 12 amino acids or less. By "synthetic peptide" is meant a peptide that is synthesized by in vitro or recombinant methods, as opposed to a peptide which is obtained by expression and processing of a gene endogenous to an organism.

The term "nucleic acids" as used herein shall be generic to polydeoxyribonucleotides (containing 2'-deoxy-D-ribose or modified forms thereof), to polyribonucleotides (containing D-ribose or modified forms thereof), and to any other type of polynucleotide which is an N-glycoside of purine or pyrimidine bases, or modified purine or pyrimidine bases.

The term "aptamer" as used herein is a single-stranded or double-stranded oligodeoxyribonucleotide, oligoribonucleotide or modified derivatives that specifically bind and alter the biological function of a target molecule. The target molecule is defined as a protein, peptide and derivatives thereof. The aptamer is capable of binding the target molecule under physiological conditions. An aptamer effect is distinguished from an antisense effect in that the aptameric effects are induced by binding to the protein, peptide and derivative thereof and are not induced by interaction or binding under physiological conditions with nucleic acid.

The term "polysaccharide" as used herein refers to a molecule comprising more than 10 glycosidically linked monosaccharide residues, while the term "oligosaccharide" refers to a molecule comprising from 2-10 glycosidically linked monosaccharide residues.

The term "small molecule" includes any molecule having a molecular weight less than about 5,000 daltons (Da), preferably less than about 2,500 Da, more preferably less than 1,000 Da, most preferably less than about 500 Da.

CPRRPYIL (SEQ ID NO: 1) Peptides

As described herein, the binding of the specific binding reagent to the CPRRPYIL (SEQ ID NO: 1) peptide is used to normalize or otherwise modulate an assay result. The term "CPRRPYIL (SEQ ID NO: 1) peptide" is used herein to refer to a synthetic peptide comprising the sequence CPRRPYIL (SEQ ID NO: 1), and one or more synthetic peptides having at least 87.5% homology to the sequence CPRRPYIL (SEQ ID NO: 1) over a contiguous 8 residue stretch. An example of an analog of this sequence falling within the definition of a CPRRPYIL (SEQ ID NO: 1) peptide is the sequence KPRRPYIL (SEQ ID NO: 5), which represents residues 156-163 of human Neurotensin (Swiss-Prot P30990)(SEQ ID NO: 3):

```
        10         20         30         40         50         60
MMAGMKIQLV CMLLLAFSSW SLCSDSEEEM KALEADFLTN MHTSKISKAH VPSWKMTLLN 70         80         90        100        110        120
VCSLVNNLNS PAEETGEVHE EELVARRKLP TALDGFSLEA MLTIYQLHKI CHSRAFQHWE 130        140        150        160        170
LIQEDILDTG NDKNGKEEVI KRKIPYILKR QLYENKPRRP YILKRDSYYY
```

ELAGLGFAELQC (SEQ ID NO: 4) Peptides

As described herein, the binding of the specific binding reagent to the ELAGLGFAELQC (SEQ ID NO: 4) peptide is used to normalize or otherwise modulate an assay result. The term "ELAGLGFAELQC (SEQ ID NO: 4) peptide" is used herein to refer to a synthetic peptide comprising the sequence ELAGLGFAELQC (SEQ ID NO: 4), and one or more synthetic peptides having at least 87.5% homology to the sequence ELAGLGFAELQC (SEQ ID NO: 4) over a contiguous 8 residue stretch. An example of an analog of this sequence falling within the definition of a ELAGLGFAELQC (SEQ ID NO: 4) peptide is the sequence ELAGLGFAELQD (SEQ ID NO: 6), which represents residues 84-95 of human Troponin I from cardiac muscle (Swiss-Prot P19429) (SEQ ID NO: 7):

```
        10         20         30         40         50         60
MADGSSDAAR EPRPAPAPIR RRSSNYRAYA TEPHAKKKSK ISASRKLQLK TLLLQIAKQE 70         80         90        100        110        120
LEREAEERRG EKGRALSTRC QPLELAGLGF AELQDLCRQL HARVDKVDEE RYDIEAKVTK 130        140        150        160        170        180
NITEIADLTQ KIFDLRGKFK RPTLRRVRIS ADAMMQALLG ARAKESLDLR AHLKQVKKED 190        200        210
TEKENREVGD WRKNIDALSG MEGRKKKFES
```

CDWRKNIDAL (SEQ ID NO: 8) Peptides

As described herein, the binding of the specific binding reagent to the CDWRKNIDAL (SEQ ID NO: 8) peptide is used to normalize or otherwise modulate an assay result. The term "CDWRKNIDAL (SEQ ID NO: 8) peptide" is used herein to refer to a synthetic peptide comprising the sequence CDWRKNIDAL (SEQ ID NO: 8), and one or more synthetic peptides having at least 87.5% homology to the sequence CDWRKNIDAL (SEQ ID NO: 8) over a contiguous 8 residue stretch. An example of an analog of this sequence falling within the definition of a CDWRKNIDAL (SEQ ID NO: 8) peptide is the sequence GDWRKNIDAL (SEQ ID NO: 9), which represents residues 189-198 of human Troponin I from cardiac muscle (Swiss-Prot P19429) (SEQ ID NO: 7):

```
        10         20         30         40         50         60
MADGSSDAAR EPRPAPAPIR RRSSNYRAYA TEPHAKKKSK ISASRKLQLK TLLLQIAKQE 70         80         90        100        110        120
LEREAEERRG EKGRALSTRC QPLELAGLGF AELQDLCRQL HARVDKVDEE RYDIEAKVTK 130        140        150        160        170        180
NITEIADLTQ KIFDLRGKFK RPTLRRVRIS ADAMMQALLG ARAKESLDLR AHLKQVKKED 190        200        210
TEKENREVGD WRKNIDALSG MEGRKKKFES
```

CPRRPYIL (SEQ ID NO: 1), ELAGLGFAELQC (SEQ ID NO: 4) and CDWRKNIDAL (SEQ ID NO: 8) peptides of the invention may be used to generate antibodies. The advantage of immunizing with synthetic peptides is that unlimited quantity of pure stable antigen can be used. This approach involves synthesizing short peptide sequences, coupling them to a large carrier molecule, and immunizing the animal of choice with the peptide-carrier molecule. The properties of antibodies are dependent on the primary sequence information. A good response to the desired peptide usually can be generated with careful selection of the sequence and coupling method. Most coupling methods rely on the reactive functional groups in amino acids, such as —NH2, —COOH, —SH, and phenolic —OH. Exemplary coupling methods are described hereinafter.

Small molecules such as the CPRRPYIL (SEQ ID NO: 1), ELAGLGFAELQC (SEQ ID NO: 4) and CDWRKNIDAL (SEQ ID NO: 8) peptides of the invention are not usually immunogenic, even when administered in the presence of adjuvant. In order to generate an immune response to these compounds, it is often necessary to attach them to a protein or other compound, termed a carrier, that is immunogenic. When attached to a carrier protein the small molecule immunogen is called a hapten. Haptens are also conjugated to carrier proteins for use in immunoassays. The carrier protein provides a means of attaching the hapten to a solid support such as a microtiter plate or nitrocellulose membrane. When attached to agarose they may be used for purification of the anti-hapten antibodies. They may also be used to create a multivalent antigen that will be able to form large antigen-antibody complexes. When choosing carrier proteins, remember that the animal will form antibodies to the carrier protein as well as to the attached hapten. It is therefore important to select a carrier protein for immunization that is unrelated to proteins that may be found in the assay sample. If haptens are being conjugated for both immunization and assay, the two carrier proteins should be as different as possible. This allows the antiserum to be used without having to isolate the anti-hapten antibodies from the anti-carrier antibodies.

Keyhole limpet hemocyanin (KLH) is a respiratory protein found in mollusks. Its large size makes it very immunogenic, and the large number of lysine residues available for conjugation make it very useful as a carrier for small peptides such as the CPRRPYIL (SEQ ID NO: peptides of the invention. The phylogenic separation between mammals and mollusks increases the immunogenicity and reduces the risk of cross-reactivity between antibodies against the KLH carrier and naturally occurring proteins in mammalian samples.

Binding Reagents

Preferably, an antibody or other binding partner used in an assay is selected that specifically binds a marker of interest, in this case a CPRRPYIL (SEQ ID NO: 1) peptide, and that does not bind to certain undesired non-target molecules which may be present in samples. The term "specifically binds" is not intended to indicate that an antibody/binding partner binds exclusively to its intended target. Rather, an antibody/binding partner "specifically binds" if its affinity for its intended target is about 5-fold greater when compared to its affinity for a non-target molecule. Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Specific binding between an antibody or other binding agent and an antigen means a binding affinity of at least 106 M-1. Preferred antibodies bind with affinities of at least about 107 M-1, and preferably between about 108 M-1 to about 109 M-1, about 109 M-1 to about 1010 M-1, or about 1010 M-1 to about 1011 M-1.

Affinity is calculated as $K_d = k_{off}/k_{on}$ ($k_{off}$ is the dissociation rate constant, $k_{on}$ is the association rate constant and $K_d$ is the equilibrium constant Affinity can be determined at equilibrium by measuring the fraction bound (r) of labeled ligand at various concentrations (c). The data are graphed using the Scatchard equation: r/c=K(n−r):

where
r=moles of bound ligand/mole of receptor at equilibrium;
c=free ligand concentration at equilibrium;
K=equilibrium association constant; and
n=number of ligand binding sites per receptor molecule By graphical analysis, r/c is plotted on the Y-axis versus r on the X-axis thus producing a Scatchard plot. The affinity is the negative slope of the line. $k_{off}$ can be determined by competing bound labeled ligand with unlabeled excess ligand (see, e.g., U.S. Pat. No. 6,316,409). The affinity of a targeting agent for its target molecule is preferably at least about $1 \times 10^{-6}$ moles/liter, is more preferably at least about $1 \times 10^{-7}$ moles/liter, is even more preferably at least about $1 \times 10^{-8}$ moles/liter, is yet even more preferably at least about $1 \times 10^{-9}$ moles/liter, and is most preferably at least about $1 \times 10^{-10}$ moles/liter. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The generation and selection of antibodies may be accomplished several ways. For example, one way is to purify polypeptides of interest or to synthesize the polypeptides of interest using, e.g., solid phase peptide synthesis methods well known in the art. See, e.g., Guide to Protein Purification, Murray P. Deutcher, ed., Meth. Enzymol. Vol 182 (1990); Solid Phase Peptide Synthesis, Greg B. Fields ed., Meth. Enzymol. Vol 289 (1997); Kiso et al., Chem. Pharm. Bull. (Tokyo) 38: 1192-99, 1990; Mostafavi et al., Biomed. Pept. Proteins Nucleic Acids 1: 255-60, 1995; Fujiwara et al., Chem. Pharm. Bull. (Tokyo) 44: 1326-31, 1996. The selected polypeptides may then be injected, for example, into mice or rabbits, to generate polyclonal or monoclonal antibodies. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)).

In addition, numerous publications have reported the use of phage display technology to produce and screen libraries of polypeptides for binding to a selected target. See, e.g., Cwirla et al., Proc. Natl. Acad. Sci. USA 87, 6378-82, 1990; Devlin et al., Science 249, 404-6, 1990, Scott and Smith, Science 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

Alternatively, to optimize the capture of antigen-specific phage and minimize the binding of irrelevant phage antibodies, a simultaneous positive and negative selection strategy is employed. In this case, a competition is set up between a small quantity of antigen (e.g. on a cell surface, magnetic particle, other solid phase, etc.) and an excess quantity of the undesired cross-reactant that serves as a sink for the non-specific adherence of irrelevant phage antibodies. By way of example, cells bearing the antigen of interest (a CPRRPYIL (SEQ ID NO: 1) peptide) may be diluted into an excess of the undesired cross-reactant fibrinogen. Following incubation of the cell admixture with a phage library, the antigen-positive cell population is retrieved and phage encoding antigen-specific antibodies are eluted and propagated in bacterial culture.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Those skilled in the art will recognize that many approaches can be taken in producing antibodies or binding fragments and screening and selecting for affinity and specificity for the various polypeptides, but these approaches do not change the scope of the invention.

In addition to antibodies, other specific binding species that do not rely on an immunoglobulin scaffold may be used in lieu thereof. By way of example, nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms Peptide aptamers are proteins that are designed to interfere with other protein interactions inside cells. They consist of a variable peptide loop attached at both ends to a protein scaffold. This double structural constraint greatly increases the binding affinity of the peptide aptamer to levels comparable to an antibody's (nanomolar range). Aptamers are useful in biotechnological and therapeutic applications as they offer molecular recognition properties that rival that of the commonly used biomolecule, antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. Since the discovery of aptamers, many researchers have used aptamer selection as a means for generation of suitable binding partners for binding assay.

CPRRPYIL (SEQ ID NO: 1), ELAGLGFAELQC (SEQ ID NO: 4) and CDWRKNIDAL (SEQ ID NO: 8) peptides and binding reagents in immunoassay controls.

The CPRRPYIL (SEQ ID NO: 1), ELAGLGFAELQC (SEQ ID NO: 4) and CDWRKNIDAL (SEQ ID NO: 8) peptides and their corresponding binding reagents may be used as assay controls in any immunoassay format. Essentially, the reagents serve as a binding pair which, when mixed with a sample matrix, react similarly to the analyte assay(s) of interest, in that the binding of a CPRRPYIL (SEQ ID NO: 1), ELAGLGFAELQC (SEQ ID NO: 4) or CDWRKNIDAL (SEQ ID NO: 8) peptide to its corresponding binding partner is exposed to the same sample matrix, temperature, storage conditions, etc., as the analyte assay.

In one example, a test device is used to detect the presence or amount of "analyte A." A peptide comprising the sequence CPRRPYIL (SEQ ID NO: 1) and/or ELAGLGFAELQC (SEQ ID NO: 4) and/or CDWRKNIDAL (SEQ ID NO: 8) is detectably labeled, and antibodies or other binding reagents that specifically bind to SEQ ID NO: 1, SEQ ID NO: 4 or SEQ ID NO: 8, respectively, are immobilized at a "control capture zone" on a solid phase. The control capture zone is positioned such that it is closely adjacent to an analyte capture zone (e.g., a location on the solid phase at which an "analyte capture reagent" such as an antibody to analyte A is immobilized to analyte A is immobilized) so that the conditions of the assay are similar (e.g., essentially the same) at both the control capture zone and the analyte capture zone.

In an alternative embodiment, a test device is used to detect the presence or amount of "analyte B." A peptide comprising or consisting of the sequence CPRRPYIL (SEQ ID NO: 1) and/or ELAGLGFAELQC (SEQ ID NO: 4) and/or CDWRKNIDAL (SEQ ID NO: 8) is immobilized at a "control capture zone" on a solid phase, while antibodies or other binding reagents that specifically bind to SEQ ID NO: 1, SEQ ID NO: 4 or SEQ ID NO: 8, respectively, are detectably labeled. The control capture zone is positioned such that it is closely adjacent to an analyte capture zone (e.g., a location on the solid phase at which an "analyte capture reagent" such as an antibody to analyte B is immobilized) so that the conditions of the assay are similar (e.g., essentially the same) at both the control capture zone and the analyte capture zone.

In each case, the detectably labeled member of the CPRRPYIL (SEQ ID NO: 1) peptide/binding reagent pair and/or ELAGLGFAELQC (SEQ ID NO: 4) peptide/binding reagent pair and/or CDWRKNIDAL (SEQ ID NO: 8) peptide/binding reagent pair is mixed with the sample to be analyzed, and then applied to the test device such that it contacts the control capture zone and analyte capture zone. An assay signal is developed from the analyte capture zone which is related to the presence or amount of the analyte, and a control signal is developed from the control capture zone which is related to the binding of the CPRRPYIL (SEQ ID NO: 1) peptide and/or ELAGLGFAELQC (SEQ ID NO: 4) peptide and/or CDWRKNIDAL (SEQ ID NO: 8) peptide to its binding reagent. The signals are detected using an appropriate means for the type of label employed. In a preferred embodiment, the amount is detected by an optical method, such as by measuring the amount of fluorescence of the label of the analyte binding particles. Alternatively, signals can be detected using electrical conductivity or dielectric (capacitance). Alternatively, electrochemical detection of released electroactive agents, such as indium, bismuth, gallium or tellurium ions, as described by Hayes et al. (Analytical Chem. 66:1860-1865 (1994)) or ferrocyanide as suggested by Roberts and Durst (Analytical Chem. 67:482-491 (1995)) can be used.

Specific peptides and binding reagents in immunoassay controls

An immunoassay may be performed wherein a predefined conjugate of a carrier and synthetic peptide which represents an epitope of interest for a target analyte is prepared and immobilized to a location downstream of a test location within an assay device. The carrier conjugate is configured in such a way that one or more synthetic epitopes are presented at the surface of the diagnostic test lane through which sample mixed with labelled detection antibody is flowed. Any labelled detection antibody that has not bound to target present in the sample will flow along the test lane where it may bind to the one or more synthetic epitopes presented on carrier conjugate which is immobilized at a solid phase location downstream of the test zone.

The use of such a synthetic epitopes downstream of a test spot will generate a signal indicating (i) that labelled capture antibody was successfully rehydrated and suspended in sample fluid and (ii) that the antibody of the labelled capture antibody is bioactive and functional. Accordingly the implementation of such a positive control arrangement in an assay device gives confidence that the specified reagents are performing as expected.

In an assay for human cardiac troponin I (hcTnI), a synthetic peptide having amino acid sequence ELAGLGFAELQC (SEQ ID NO: 4) which is representative of amino acid region 84-94 of hcTnI, may be synthesized and incorporated into the assay. Optionally or additionally, a synthetic peptide having amino acid sequence CDWRKNIDAL (SEQ ID NO: 8) which is representative of amino acid region 190-198 of hcTnI may be synthesized and incorporated into the assay. The synthetic ELAGLGFAELQC (SEQ ID NO: 4) and/or CDWRKNIDAL (SEQ ID NO: 8) peptides are conjugated to a suitable carrier protein, such as for example human serum albumin, using standard peptide immobilization chemistry techniques. The carrier protein is subsequently immobilized within the test lane of an assay device downstream (that is at a distance further along the test lane that sample fluid migrates to where sample is first applied)

of a region to which an anti-hcTnI antibody, which recognizes a different epitope region, such as for example amino acids 27-39 and 34-55 of hcTnI (the capture antibodies) have been immobilized.

An antibody directed against amino acid region 84-94 or amino acid region 190-198, which is conjugated to a detectable label, is used in the immunoassay. Examples of suitable labels include an enzyme, a fluorescent label, a radionuclide, an electrochemically active species, a chemiluminescent species, a colloidal sol particle, such as a gold sol or a latex particle. In some embodiments the label is a fluorescence energy transfer latex (FETL) particle. The detection antibody is capable of simultaneously binding to hcTnI which has been bound by the capture antibody. As such, amino acid regions 27-39/34-55 and 84-94 or 190-198 are sufficiently spatially separated that steric hindrance does not occur when the capture antibody and detection antibody are both bound to hcTnI.

FIG. 1 depicts an assay device of an exemplary embodiment, comprising an assay test spot configured to detect the presence of hcTnI (TnI spot) along with a specific control spot (Preconjugated peptide spot) that is downstream of the test spot with respect to flow of a test sample along a diagnostic lane. The test spot comprises an immobilized capture antibody directed against amino acid region 27-39/34-55 of hcTnI. The control spot comprises a conjugate consisting of a synthetic peptide with amino acid sequence ELAGLGFAELQC (SEQ ID NO: 4) covalently couple to a human serum albumin carrier (HSA) protein. The CPRRPYIL (SEQ ID NO: 1) peptide and CDWRKNIDAL (SEQ ID NO: 8) peptide would be used in a similar fashion.

Sample fluid, such as for example blood, serum, plasma, urine, saliva, ejaculate, cerebrospinal fluid, suspected of containing the target of interest (hcTnI) is applied to a test device at an upstream location. Within the upstream location is provided an excess amount of dried down detection antibody, which is solubilized by the sample fluid. The detection antibody subsequently interact with and binds to any target present within the sample. The labeled sample thereafter flows along the diagnostic lane. The sample initially contacts the test spot, wherein target may interact with and be captured on the immobilized capture antibody. As sample fluid continues along the diagnostic lane, excess detection antibody interacts with and binds the synthetic peptide that is immobilized to the control spot.

Detectable signals thus develop at both the test and control spots respectively. The intensity of the signal at the test spot is indicative of the presence or amount of target present in the sample fluid. The presence of signal at the control is indicative that (i) sufficient sample was applied to the device to cause resuspension of the dried detection antibody and carry same along past the test spot to the control spot, and (ii) that the detection antibody is bioactive and capable of binding target.

Correction of Assay Signals

Correction of the assay signal using the control signal using methods such as those described in U.S. Pat. Nos. 5,356,782, 5,753,517, 7,691,595, and 7,713,703. In one example, a corrected assay signal may be determined according to the following equation:

$$\text{Normalized assay signal} = A * (\text{Signal}_{Assay}) / \text{Signal}_{Control}$$

In another example, a corrected assay signal may be determined according to the following equation:

$$\text{Normalized assay signal} = A * (\text{Signal}_{Assay})^{B3} / (\text{Signal}_{Control\ 1}^{B1} * \text{Signal}_{Control\ 2}^{B2})$$

As noted above, assays such as immunoassays require methods for detection, and one of the most common methods for quantitation of results is to conjugate an enzyme, fluorophore or other molecule to form an antibody-label conjugate. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.). Particularly preferred detectable labels are fluorescent latex particles such as those described in U.S. Pat. Nos. 5,763,189, 6,238,931, and 6,251,687; and International Publication WO95/08772, each of which is hereby incorporated by reference in its entirety. Exemplary conjugation to such particles is described hereinafter. Direct labels include fluorescent or luminescent tags, metals, dyes, radionuclides, and the like, attached to the antibody. Indirect labels include various enzymes well known in the art, such as alkaline phosphatase, horseradish peroxidase and the like.

Solid-Phase Immobilization

As also noted above, assays such as immunoassays often rely on reagents immobilized on solid-phase matrices for use as affinity supports or for sample analysis. Thus, antibodies or their binding fragments, CPRRPYIL (SEQ ID NO: 1) peptides, ELAGLGFAELQC (SEQ ID NO: 4) peptides, CDWRKNIDAL (SEQ ID NO: 8) peptides, etc., can be immobilized on solid-phase matrices. The term "solid phase" as used herein refers to a wide variety of materials including solids, semi-solids, gels, films, membranes, meshes, felts, composites, particles, papers and the like typically used by those of skill in the art to sequester molecules. The solid phase can be non-porous or porous. Suitable solid phases include those developed and/or used as solid phases in solid phase binding assays. See, e.g., chapter 9 of Immunoassay, E. P. Dianiandis and T. K. Christopoulos eds., Academic Press: New York, 1996, hereby incorporated by reference. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. See, e.g., Leon et al., Bioorg. Med. Chem. Lett. 8: 2997, 1998; Kessler et al., Agnew. Chem. Int. Ed. 40: 165, 2001; Smith et al., J. Comb. Med. 1: 326, 1999; Orain et al., Tetrahedron Lett. 42: 515, 2001; Papanikos et al., J. Am. Chem. Soc. 123: 2176, 2001; Gottschling et al., Bioorg. Med. Chem. Lett. 11: 2997, 2001.

Surfaces such as those described above may be modified to provide linkage sites, for example by bromoacetylation, silation, addition of amino groups using nitric acid, and attachment of intermediary proteins, dendrimers and/or star polymers. This list is not meant to be limiting, and any method known to those of skill in the art may be employed.

Coupling of Reagents

Chemical cross-linkers are valuable tools for preparing antibody-detectable label conjugates, antigenic constructs, immunotoxins and other labeled protein and nucleic acid reagents. These reagents may be classified on the basis of the following:

1. Functional groups and chemical specificity;
2. length and composition of the cross-bridge;
3. whether the cross-linking groups are similar (homobifunctional) or different (heterobifunctional);
4. whether the groups react chemically or photochemically;
5. whether the reagent is cleavable; and
6. whether the reagent can be radiolabeled or tagged with another label.

As the cysteine residue of the CPRRPYIL (SEQ ID NO: 1), ELAGLGFAELQC (SEQ ID NO: 4) and CDWRKNIDAL (SEQ ID NO: 8) peptides of the present invention provide an available thiol to act as an attachment point, targets may be prepared to provide an appropriate thiol-reactive site. Cross-linking reagents that couple through sulfhydryls (thiols) are available from many commercial sources. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Such reagents may be bifunctional, in that a second site on the reagent is available for use in modifying a conjugation target to incorporate the thiol-reactive site. In addition to thiols, reactive groups that can be targeted using a cross-linker include primary amines, carbonyls, carbohydrates and carboxylic acids. In addition, many reactive groups can be coupled nonselectively using a cross-linker such as photoreactive phenyl azides. For suitable reagents, see Pierce 2003-2004 Applications Handbook and Catalog #1600926, which is hereby incorporated by reference. Cross-linkers that are amine-reactive at one end and sulfhydryl-reactive at the other end are quite common. If using heterobifunctional reagents, the most labile group is typically reacted first to ensure effective cross-linking and avoid unwanted polymerization.

Many factors must be considered to determine optimum cross-linker-to-target molar ratios. Depending on the application, the degree of conjugation is an important factor. For example, when preparing immunogen conjugates, a high degree of conjugation is normally desired to increase the immunogenicity of the antigen. However, when conjugating to an antibody or an enzyme, a low-to-moderate degree of conjugation may be optimal to ensure that the biological activity of the protein is retained. It is also important to consider the number of reactive groups on the surface of the protein. If there are numerous target groups, a lower cross-linker-to-protein ratio can be used. For a limited number of potential targets, a higher cross-linker-to-protein ratio may be required. This translates into more cross-linker per gram for a small molecular weight protein.

Conformational changes of proteins associated with a particular interaction may also be analyzed by performing cross-linking studies before and after the interaction. A comparison is made by using different arm-length cross-linkers and analyzing the success of conjugation. The use of cross-linkers with different reactive groups and/or spacer arms may be desirable when the conformation of the protein changes such that hindered amino acids become available for cross-linking.

Cross-linkers are available with varying lengths of spacer arms or bridges connecting the reactive ends. The most apparent attribute of the bridge is its ability to deal with steric considerations of the moieties to be linked. Because steric effects dictate the distance between potential reaction sites for cross-linking, different lengths of bridges may be considered for the interaction. Shorter spacer arms are often used in intramolecular cross-linking studies, while intermolecular cross-linking is favored with a cross-linker containing a longer spacer arm.

The inclusion of polymer portions (e.g., polyethylene glycol ("PEG") homopolymers, polypropylene glycol homopolymers, other alkyl-polyethylene oxides, bis-polyethylene oxides and co-polymers or block co-polymers of poly(alkylene oxides)) in cross-linkers can, under certain circumstances be advantageous. See, e.g., U.S. Pat. Nos. 5,643,575, 5,672,662, 5,705,153, 5,730,990, 5,902,588, and 5,932,462; and Topchieva et al., Bioconjug. Chem. 6: 380-8, 1995). For example, U.S. Pat. No. 5,672,662 discloses bifunctional cross-linkers comprising a PEG polymer portion and a single ester linkage. Such molecules are said to provide a half-life of about 10 to 25 minutes in water.

Designing a cross-linker involves selection of the functional moieties to be employed. The choice of functional moieties is entirely dependent upon the target sites available on the species to be crosslinked. Some species (e.g., proteins) may present a number of available sites for targeting (e.g., lysine ε-amino groups, cysteine sulfhydryl groups, glutamic acid carboxyl groups, etc.), and selection of a particular functional moiety may be made empirically in order to best preserve a biological property of interest (e.g., binding affinity of an antibody, catalytic activity of an enzyme, etc.)

1. Coupling Through Amine Groups

Imidoester and N-hydroxysuccinimidyl ("NHS") esters are typically employed as amine-specific functional moieties. NHS esters yield stable products upon reaction with primary or secondary amines. Coupling is efficient at physiological pH, and NHS-ester cross-linkers are more stable in solution than their imidate counterparts. Homobifunctional NHS-ester conjugations are commonly used to cross-link amine-containing proteins in either one-step or two-step reactions. Primary amines are the principle targets for NHS-esters. Accessible α-amine groups present on the N-termini of proteins react with NHS-esters to form amides. However, because α-amines on a protein are not always available, the reaction with side chains of amino acids become important. While five amino acids have nitrogen in their side chains, only the ε-amino group of lysine reacts significantly with NHS-esters. A covalent amide bond is formed when the NHS-ester cross-linking agent reacts with primary amines, releasing N-hydroxysuccinimide 2. Coupling Through Sulfhydryl Groups Maleimides, alkyl and aryl halides, α-haloacyls, and pyridyl disulfides are typically employed as sulfhydryl-specific functional moieties. The maleimide group is specific for sulfhydryl groups when the pH of the reaction mixture is kept between pH 6.5 and 7.5. At pH 7, the reaction of the maleimides with sulfhydryls is 1000-fold faster than with amines. Maleimides do not react with tyrosines, histidines or methionines. When free sulfhydryls are not present in sufficient quantities, they can often be generated by reduction of available disulfide bonds.

3. Coupling Through Carboxyl Groups

Carbodiimides couple carboxyls to primary amines or hydrazides, resulting in formation of amide or hydrazone bonds. Carbodiimides are unlike other conjugation reactions in that no cross-bridge is formed between the carbodiimide and the molecules being coupled; rather, a peptide bond is formed between an available carboxyl group and an available amine group. Carboxy termini of proteins can be targeted, as well as glutamic and aspartic acid side chains. In the presence of excess cross-linker, polymerization may occur because proteins contain both carboxyls and amines. No cross-bridge is formed, and the amide bond is the same as a peptide bond, so reversal of the cross-linking is impossible without destruction of the protein.

4. Nonselective Labeling

A photoaffinity reagent is a compound that is chemically inert but becomes reactive when exposed to ultraviolet or visible light. Arylazides are photoaffinity reagents that are photolyzed at wavelengths between 250-460 nm, forming a reactive aryl nitrene. The aryl nitrene reacts nonselectively to form a covalent bond. Reducing agents must be used with caution because they can reduce the azido group.

5. Carbonyl Specific Cross-Linkers

Carbonyls (aldehydes and ketones) react with amines and hydrazides at pH 5-7. The reaction with hydrazides is faster than with amines, making this useful for site-specific cross-linking. Carbonyls do not readily exist in proteins; however, mild oxidation of sugar moieties using sodium metaperiodate will convert vicinal hydroxyls to aldehydes or ketones.

Assay Systems

Numerous methods and devices are well known to the skilled artisan for the practice of receptor binding assays. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety, including all tables, figures and claims. These devices and methods can utilize detectably labeled molecules and antibody solid phases in various sandwich, competitive, or non-competitive assay formats, to generate a signal that is related to the presence or amount of an analyte of interest. One skilled in the art also recognizes that robotic instrumentation including but not limited to Beckman Access, Abbott AxSym, Roche ElecSys, Dade Behring Stratus systems are among the immunoassay analyzers that are capable of performing such immunoassays. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. As described herein, preferred assays utilize an antibody raised against a CPRRPYIL (SEQ ID NO: 1) peptide.

In its simplest form, an assay device according to the invention may comprise a solid surface comprising receptor(s) that specifically bind one or more analytes of interest. For example, antibodies may be immobilized onto a variety of solid supports, such as magnetic or chromatographic matrix particles, the surface of an assay plate (such as microtiter wells), pieces of a solid substrate material or membrane (such as plastic, nylon, paper), and the like using the cross-linkers of the present invention. The analysis of a plurality of analytes may be carried out separately or simultaneously with one test sample. For separate or sequential assay of markers, suitable apparatuses include clinical laboratory analyzers such as the ElecSys (Roche), the AxSym (Abbott), the Access (Beckman), the ADVIA® CENTAUR® (Bayer) immunoassay systems, the NICHOLS ADVANTAGE® (Nichols Institute) immunoassay system, etc. Preferred apparatuses or protein chips perform simultaneous assays of a plurality of analytes on a single surface. Particularly useful physical formats comprise surfaces having a plurality of discrete, addressable locations for the detection of a plurality of different analytes. Such formats include protein microarrays, or "protein chips" (see, e.g., Ng and Ilag, *J. Cell Mal. Med.* 6: 329-340 (2002)) and certain capillary devices (see, e.g., U.S. Pat. No. 6,019,944). In these embodiments, each discrete surface location may comprise antibodies to immobilize one or more analyte(s) (e.g., a marker) for detection at each location. Surfaces may alternatively comprise one or more discrete particles (e.g., microparticles or nanoparticles) immobilized at discrete locations of a surface, where the microparticles comprise antibodies to immobilize one analyte (e.g., a marker) for detection.

EXAMPLES

The following examples serve to illustrate the present invention. These examples are in no way intended to limit the scope of the invention.

Example 1. PLYENKPRRPYILC (SEQ ID NO: 2) and CPRRPYIL (SEQ ID NO: 1) Peptide Conjugates Keyhole Limpet Hemocyanin (KLH, Calbiochem #374817, 50 mg/mL in glycerol) was passed through a 40 mL GH25 column equilibrated in 0.1M potassium phosphate, 0.1M borate, 0.15M sodium chloride buffer, pH 7.5 to remove glycerol. A 1.5-fold molar excess of N-ethylmaleimide was added, and the mixture incubated 30 minutes at room temperature. A 200-fold molar excess of sulfo-SMCC (Pierce #22322) from a 50 mM stock in distilled water was added while vortexing. Vortexing was continued for another 30 seconds, followed by incubation for 10 minutes at room temperature. A 100-fold molar excess of SMCC (Pierce #22360) from an 80 mM stock in acetonitrile was added while vortexing. 1M KOH was added to maintain a pH of between 7.2 and 7.4. The mixture was stirred at room temperature for 90 minutes. After 90 minutes incubation, KLH-SMCC was purified by gel filtration using a GH25 column equilibrated in 0.1M potassium phosphate, 0.02M borate, 0.15M sodium chloride buffer, pH 7.0.

Peptide-Keyhole Limpet Hemocyanin (KLH) conjugates were made essentially as described in Example 21 of U.S. Pat. No. 6,057,098 with the following modifications: KLH-SMCC was reacted with a 2-fold excess of peptide and 5% each of PADRE (peptide 1024.03 from Alexander et al., *Immunity* 1: 751-761, 1994).

Bovine Serum Albumin (BSA) conjugates with peptide were made essentially as described in Example 21 of U.S. Pat. No. 6,057,098. The BSA biotin peptide conjugates were made by first biotinylating the BSA (Example 9 of U.S. Pat. No. 6,057,098), then conjugating with peptide using SMCC. For phage display panning as described below, PLYENKPRRPYILC (SEQ ID NO: 2) conjugated to BSA-SMCC was used.

Example 2. Magnetic Latex Particles

Magnetic latex (Estapor, 10% solids, Bangs Laboratories, Fishers, Ind.) was thoroughly resuspended and 2 ml aliquoted into a 15 ml conical tube. The magnetic latex was suspended in 12 ml distilled water and separated from the solution for 10 min using a magnet. While still in the magnet, the liquid was carefully removed with a 10 mL sterile pipet. This washing process was repeated three times. After the final wash, the latex was resuspended in 2 ml of distilled water. In a separate 50 ml conical tube, 10 mg of avidin-HS (NeutrAvidin, Pierce, Rockford, Ill.) was dissolved in 18 ml of 40 mM Tris, 0.15 M sodium chloride, pH 7.5 (TBS). While vortexing, the 2 ml of washed magnetic latex was added to the diluted avidin-HS and the mixture vortexed an additional 30 seconds. This mixture was incubated at 45° C. for 2 hr, shaking every 30 minutes. The avidin magnetic latex was separated from the solution using a magnet and washed three times with 20 ml BBS as described above. After the final wash, the latex was resuspended in 10 ml BBS and stored at 4° C. Immediately prior to use, the avidin magnetic latex was equilibrated in panning buffer (40 mM TRIS, 150 mM NaCl, 20 mg/mL BSA, 0.1% Tween 20 (Fisher Scientific, Pittsburgh, Pa.), pH 7.5). The avidin magnetic latex needed for a panning experiment (200 µl/sample) was added to a sterile 15 ml centrifuge tube and brought to 10 ml with panning buffer. The tube was placed on the magnet for 10 min to separate the latex. The solution was carefully removed with a 10 mL sterile pipet as described above. The magnetic latex was resuspended in 10 mL of panning buffer to begin the second wash. The magnetic latex was washed a total of 3 times with panning buffer. After the final wash, the latex was resuspended in panning buffer to the initial aliquot volume.

Example 3. Selection of Phage Expressing Anti-PLYENKPRRPYILC Antibodies and Selection of Monoclonal Fab to PLYENKPRRPYILC The first round antibody phage were generally prepared as described in Example 7 of U.S. Pat. No. 6,057,098 from RNA isolated from mice immunized with PLYEN-KPRRPYILC (SEQ ID NO: 2) conjugated to KLH and PADRE (pan-DR T-helper epitope). The antibody phage samples were panned with Dynal M-280 streptavidin magnetic latex (Life Technologies, Carlsbad) generally as described in Example 16 of U.S. Pat. No. 6,057,098. The first round antibody phage samples (10 samples from 5 different spleens) were selected using PLYENKPRRPYILC (SEQ ID NO: 2) conjugated to BSA-SMCC-biotin at a $2 \times 10^{-9}$ M final BSA concentration, with $9 \times 10^{-7}$ M BSA-SMCC added to remove antibodies specific to the SMCC arm. The eluted second round phage were enriched with 7F11 magnetic latex (Example 22 of U.S. Pat. No. 6,057,098), then the enriched phage was panned a second time with at a $2 \times 10^{-9}$ M final BSA-peptide biotin concentration and $9 \times 10^{-7}$ M BSA-SMCC. The phage eluted from the second round of panning were pooled, and the third round of panning was done with a $2 \times 10^{-9}$ M final BSA peptide biotin concentration. The selected phage were subcloned into a plasmid expression vector generally as described in Example 18 of U.S. Pat. No. 6,057,098. A monoclonal antibody was selected from the subcloned library that was shown to bind the peptide at the N-terminus. That monoclonal antibody is ST0115 ZIZM 01421. That antibody was biotinylated generally as described in Example 9 of U.S. Pat. No. 6,057,098.

Example 4. Selection of Phage Expressing Anti-ELAGLGFAELQC (SEQ ID NO: 4 Antibodies and Selection of Monoclonal Antibody to ELAGLGFAELQC (SEQ ID NO: 4) where the Antibody Cross Reacts with Troponin I Complex The first round antibody phage were generally prepared as described in Example 7 of U.S. Pat. No. 6,057,098 from RNA isolated from mice immunized with ELAGLGFA-ELQC (SEQ ID NO: 4) conjugated to KLH. The antibody phage samples were panned with Dynal M-280 streptavidin magnetic latex (Life Technologies, Carlsbad) generally as described in Example 16 of U.S. Pat. No. 6,057,098. The first round antibody phage samples (4 samples from 2 different spleens) were selected using ELAGLGFAELQC (SEQ ID NO: 4) conjugated to BSA-SMCC-biotin at 1x10-9 M final BSA concentration, with $1.4 \times 10^{-6}$ M BSA-SMCC added to remove antibodies specific to the SMCC arm. The eluted second round phage was panned a second time with $1 \times 10^{-8}$ M troponin TIC complex biotin. The phage eluted from the second round of panning were pooled, and the third round of panning was done with 1x10-8 M troponin TIC complex biotin. The phage eluted from the third round of panning was panned a fourth time with $5 \times 10^{-10}$ M troponin TIC complex biotin. The selected phage were subcloned into a plasmid expression vector generally as described in Example 18 of U.S. Pat. No. 6,057,098.

Example 5. Selection of Phage Expressing Anti-CDWRKNIDAL (SEQ ID NO: 8) Antibodies and Selection of Monoclonal Antibody to CDWRKNIDAL (SEQ ID NO: 8) where the Antibody Cross Reacts with Troponin I Complex The first round antibody phage were generally prepared as described in Example 7 of U.S. Pat. No. 6,057,098 from RNA isolated from mice immunized with cardiac troponin I (Dako, Finland). The antibody phage samples were panned with Dynal M-280 streptavidin magnetic latex (Life Technologies, Carlsbad) generally as described in Example 16 of U.S. Pat. No. 6,057,098. The first round antibody phage samples (10 samples from 5 different spleens) were selected using cardiac troponin I complexed with troponin C and troponin T (TIC complex) biotin at $5 \times 10^{-9}$ M final TIC biotin concentration. The eluted second round phage was panned a second time with $1 \times 10^{-9}$ M TIC complex biotin. The phage eluted from the second round of panning were pooled, and the third round of panning was done with $1 \times 10^{-9}$ M cardiac troponin I biotin. The selected phage were subcloned into a plasmid expression vector generally as described in Example 18 of U.S. Pat. No. 6,057,098.

Example 6. Selection of Phage Expressing Anti-CPRRPYIL (SEQ ID NO: 1) Antibodies and Selection of a Monoclonal Antibody to CPRRPYIL (SEQ ID NO: 1)

The first round antibody phage were generally prepared as described in Example 7 of U.S. Pat. No. 6,057,098 from RNA isolated from mice immunized with CPRRPYIL (SEQ ID NO: 1) conjugated to KLH and PADRE (pan-DR T-helper epitope). The antibody phage samples were panned with Dynal M-280 streptavidin magnetic latex (Life Technologies, Carlsbad) generally as described in Example 2 above except the BSA peptide biotin concentration was $1 \times 10^{-9}$ M. After the second round of selections, the individual phage samples were pooled, and the pooled phage were selected using the biotinylated ST0115 ZIZM 01421 antibody at $1 \times 10^{-8}$ M and unlabeled neurotensin peptide (Bachem, Torrance) at $1 \times 10^{-9}$ M generally as described in Example 15 of U.S. Pat. No. 6,057,098. This selection was repeated a second time, and the resulting fourth round phage were subcloned into a plasmid expression vector generally as described in U.S. Pat. No. 6,057,098. The monoclonal antibody ST0128 Z7ZM 01421 was selected from the resulting set of monoclonals.

Example 7. Immunoassay Format

For sandwich immunoassays, a plasma sample was added to the microfluidic device that contains all the necessary assay reagents, including HAMA inhibitors, in dried form. The plasma passed through a filter to remove particulate matter. Plasma entered a "reaction chamber" by capillary action. This reaction chamber contained fluorescent latex particle-antibody conjugates (hereafter called FETL-antibody conjugates) appropriate to an analyte of interest, and may contain FETL-antibody conjugates to several selected analytes. The FETL-antibody conjugates dissolved into the plasma to form a reaction mixture, which was held in the reaction chamber for an incubation period (about a minute) to allow the analyte(s) of interest in the plasma to bind to the antibodies. After the incubation period, the reaction mixture moved down the detection lane by capillary action. Antibodies to the analyte(s) of interest were immobilized in discrete capture zones on the surface of a "detection lane." Analyte/antibody-FETL complexes formed in the reaction chamber were captured on an appropriate detection zone to form a sandwich complex, while unbound FETL-antibody conjugates were washed from the detection lane into a waste chamber by excess plasma. The amount of analyte/antibody-FETL complex bound on a capture zone was quantified with a fluorometer (Triage® MeterPro, Alere) by integration of the signal over the entire spot, and was related to the amount of the selected analyte in the plasma specimen. In this case, two assays were performed simultaneously on the device in two separately determined capture zones—B-type natriuretic peptide ("BNP") and galectin-3 ("Gal-3").

The meter determines a fluorescent intensity integral (or signal) for each spot that is proportional to the amount of FETL that is bound to the solid phase spot. For each analyte spot, the signal is converted into units of analyte concentration by a calibration curve. This is written in mathematical notation as follows:
X=Analyte Spot Signal (Integral)
Y=Analyte Concentration (Test Result)=R(X)

R(X) is the calibration curve of the particular analyte assay under study, equivalent to the inverse of the dose/response curve determined during the calibration of each lot of test devices. Typically the dose/response curve is sigmoidal and may be approximately linear in the measurable (reported) range of the analyte.

The calibration curve R(X) is represented as a cubic spline given some number of (X, Y) pairs (called "knots") through which R must pass. The measurable range of the assay is divided into 11 calibrator levels (A, B, C, . . . J, and Z) where Cal A is above the upper limit of the measurable range, Cal J is near (but above) the lower limit of the measurable range and Cal Z is a "blank" sample containing zero concentration of the analyte. From 5-8 knots are used to represent the calibration curve across these 11 calibrator levels.

The analyte concentration of each calibrator sample is assigned prior to calibration. During calibration, each calibrator sample (levels A-J and Z) is tested in replicate (typically 20 to 32 tests per level) on the device lot being calibrated and the mean of X0 is calculated for each level. The calibration curve is determined by aligning the means of X0 to the known calibrator concentrations.

Example 8. Assay Normalization

An assay normalization system was included within the device based on the 8 amino acid peptide sequence (CPRRPYIL; SEQ ID NO: 1) and an antibody specific to this peptide (referred to herein as "ST128"). The ST128 antibody was selected as it does not bind to the native neurotensin peptide, nor does it bind cell culture supernatants derived from human and CHO cell lines. The CPRRPYIL (SEQ ID NO: 1) peptide was positioned on an FETL in the reaction chamber of the test device, and the antibody on a unique zone in the detection lane.

The signal from the ST128 detection zone was tightly distributed in the population with a mean and standard deviation that is on the order of what can be expected based on the precision of the device alone, i.e., with minimal matrix effects, or interference.

The analyte signal and the ST128 signal were combined in a 4-parameter regression model designed to preserve the calibration curve relative to the un-normalized signal.

The purpose of assay normalization was increased precision (improved coefficient of variation, or CV") by eliminating matrix and device effects which differ between individual test devices and are not accounted for by a lot-based calibration curve. A simple "divide by" normalization can be applied by the following equation:

$$Y = A * X0 / (X1 * X2)^{1/2}$$

where A is the mean of $(X1*X2)^{1/2}$ over all replicates; X0=Analyte Spot Signal (Integral); X1=Control Spot 1 Signal (Integral); X2=Control Spot 2 Signal (Integral); Y=Normalized Analyte Signal=F(X0,X1,X2); and Analyte Concentration (Test Result)=R(Y). A simple generalization of this is $$Y = A * X0^{\beta 0} / (X1^{\beta 1} * X2^{\beta 2})$$

where (A, β0, β1, β2) are coefficients determined by ordinary least squares regression with residuals defined as $$\text{Residual} = \log(Y_{ik}) - \log(\text{Mean } X0)_k$$

where Mean is over all replicates i at each calibrator level k. The regression is performed over all calibrator levels for a given analyte. Each analyte has its own unique set of coefficients (A, β0, β1, β2) optimized for each individual lot.

The simple "divide by" normalization (with fixed coefficients β0=1, β1=0.5, β2=0.5) does not perform as well as a 4-parameter (A, β0, β1, β2) model with lot specific (and analyte specific) coefficients. For certain analytes, a "divide by" normalization was seen to actually increase the assay CV. Therefore, the normalization coefficients are improved by tuning for each analyte. More complicated models can be constructed by exploring alternative functional forms Y=F (X0,X1,X2) with additional free parameters. For example, by allowing the log of Y to be a quadratic polynomial of the form $$\ln Y = A + \beta 0 * \ln X0 + \beta 1 * \ln X1 + \beta 2 * \ln X2 + \beta 3 * \ln X0 * \ln X1 + \beta 3 * \ln X0 * \ln X2 + \beta 5 * \ln X1 * \ln X2 + \beta 6 * \ln X0 * \ln X0 + \beta 7 * \ln X1 * \ln X1 + \beta 8 * \ln X2 * \ln X2$$

where (A, β0, β1, β2, . . . β8) are 10 coefficients determined by ordinary least squares regression with the residuals previously defined. The quadratic terms, however, are of no benefit in terms of CV reduction. These considerations show that the 4-parameter (A, β0, β1, β2) model is sufficient to tune the normalization to each analyte (and each lot) with a minimum of free parameters. However, it should be noted that the specific functional form of this 4-parameter model is not the only solution. Alternative functional forms and/or alternative definitions of the residual may be used to tune the normalization for improved precision in a certain part of the measurable range, e.g., weighted towards higher concentrations as opposed to lower concentrations.

Example 9. Calculation of the Limit-of-Blank (LOB)

It is important to have a method of calculating the limit-of-blank (LOB) that is consistent with the normalization method.

Although Y is defined across the measurable range, we have excluded Cal Z in the determination of the normalization coefficients, i.e., the regression was limited to samples Cal A-J and Cal J is above the LOB.

An additional problem arises in the examination of Cal Z, because it has a mean signal of approximately zero due to background subtraction by the meter, and the functional form of the normalization model is not defined for X0<0. To calculate the LOB, the equation for Y is re-arranged as follows $$Y = A * X0^{\beta 0} / (X1^{\beta 1} * X2^{\beta 2}) = (X0/D)^{\beta 0} \text{ where } D = (X1^{\beta 1} * X2^{\beta 2} / A)^{1/\beta 0}$$

The LOB is defined as the upper 97.5th percentile of the distribution of "blank" samples (Cal Z). We therefore sample the distribution of X0/D and estimate its upper 97.5th percentile. This can be done using a parametric approximation (of normally distributed noise) to arrive at the following expression for the LOB of the normalized signal Y:

$$\text{LOB}(Y) = (1.96 * SD)^{\beta 0} \text{ where SD is standard deviation of } X0/D.$$

This can be compared directly to the LOB of the un-normalized signal X0 which is 1.96 times the standard deviation of X0 alone. The LOB increases with normalization because at Cal Z the analyte signal X0 is purely noise, un-correlated with the controls (X1, X2), so X0 is less noisy than X0/D. Although the LOB has increased with normalization, it has only increased by a multiplier between 1.05 and 1.15 times the LOB of the un-normalized system. Typically the LOB is at least 2-fold below the lower limit of the measurable (reportable) range of the assay and therefore this effect is expected to have negligible impact on the number of false elevations above the lower limit of the assay. In particular, the upper 99th percentile of the normal reference range for TNI (based on plasma, or whole blood from apparently normal healthy individuals) should be below 0.05 ng/mL for either the normalized, or un-normalized methods.

Example 10. Pre-Conjugated Solid Phase

In a further exemplary embodiment an assay was performed wherein a pre-defined conjugate of a carrier and synthetic peptide which represents the epitope of interest for a target analyte was prepared and immobilized to a location downstream of a test location within an assay device. The carrier conjugate was configured in such a way that one or more synthetic epitopes were presented at the surface of the diagnostic test lane through which sample mixed with labelled detection antibody was flowed. Any labelled detection antibody that was not bound to target present in the sample flowed along the test lane where it bound to the one or more synthetic epitopes presented on carrier conjugate which was immobilized at a solid phase location downstream of the test zone.

The use of such a synthetic epitope downstream of a test spot generated a signal indicating (i) that labelled capture antibody was successfully rehydrated and suspended in sample fluid and (ii) that the antibody of the labelled capture antibody was bioactive and functional. Accordingly the implementation of such a positive control arrangement in an assay device gave confidence that the specified reagents were performing as expected.

In an assay for human cardiac troponin I (hcTnI), a synthetic peptide having amino acid sequence ELAGLGFAELQC (SEQ ID NO: 4) which is representative of amino acid region 84-94 of hcTnI was synthesized. Optionally or additionally, a synthetic peptide having amino acid sequence CDWRKNIDAL (SEQ ID NO: 8) which is representative of amino acid region 190-198 of hcTnI was synthesized. The synthetic ELAGLGFAELQC (SEQ ID NO: 4) and/or CDWRKNIDAL (SEQ ID NO: 8) peptides were subsequently conjugated to suitable carrier protein using standard peptide immobilization chemistry techniques. The carrier protein was subsequently immobilized within the test lane of an assay device downstream of a region to which an anti-hcTnI antibody, which recognizes a different epitope region, such as for example amino acids 27-39 and 34-55 of hcTnI (the capture antibodies).

An antibody directed against amino acid region 84-94 or amino acid region 190-198 was conjugated to a detectable label. Examples of suitable labels include an enzyme, a fluorescent label, a radionuclide, an electrochemically active species, a chemiluminescent species, a colloidal sol particle, such as a gold sol or a latex particle. In some embodiments the label is a fluorescence energy transfer latex (FETL) particle. The detection antibody is capable of simultaneously binding to hcTnI which has been bound by the capture antibody. As such, amino acid regions 27-39/34-55 and 84-94 or 190-198 are sufficiently spatially separated that steric hindrance does not occur when the capture antibody and detection antibody are both bound to hcTnI.

The control spot comprises a conjugate consisting of a synthetic peptide with amino acid sequence ELAGLGFAELQC (SEQ ID NO: 4) or CDWRKNIDAL (SEQ ID NO: 8) covalently coupled to a human serum albumin carrier (HSA) protein. The HSA was subsequently immobilized to the diagnostic lane.

Sample fluid, such as for example blood, serum, plasma, urine, saliva, ejaculate, cerebrospinal fluid, suspected of containing the target of interest (hcTnI) was applied to a test device at an upstream location. Within the upstream location was provided an excess amount of dried down detection antibody, which is solubilized by the sample fluid. The detection antibody subsequently interacted with and bound to any target present within the sample. The labeled sample thereafter flowed along the diagnostic lane. The sample initially contacted the test spot, wherein target interacted with and was captured on the immobilized capture antibody. As sample fluid continued along the diagnostic lane, excess detection antibody interacted with and bound the synthetic peptide that was immobilized to the control spot.

Detectable signals developed at both the test and control spots respectively. The intensity of the signal at the test spot was indicative of the presence or amount of target present in the sample fluid. The presence of signal at the control was indicative that (i) sufficient sample was applied to the device to cause resuspension of the dried detection antibody and carry same along past the test spot to the control spot, and (ii) that the detection antibody was bioactive and capable of binding target.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A device, comprising:
   a substrate defining at least one diagnostic lane;
   a sample application zone;
   a dried reagent zone; and
   a detection zone comprising at least one control zone and at least one assay zone;
   wherein at least one of the dried reagent zone or the control zone comprises a peptide having 87.5% identify to SEQ ID No: 1.

2. The device of claim 1, wherein the control zone comprises the peptide.

3. The device of claim 2, wherein the peptide is immobilized in the control zone.

4. The device of claim 3, wherein the dried reagent zone comprises an agent conjugated to a detectable label.

5. The device of claim 1, wherein the dried reagent zone comprises the peptide.

6. The device of claim 5, wherein the peptide is conjugated to a detectable label.

7. A device, comprising:
   a substrate defining at least one diagnostic lane;
   a sample application zone;
   a dried reagent zone; and
   a detection zone comprising at least one control zone and at least one assay zone;
   wherein the at least one control zone comprises a peptide of SEQ ID NO: 1.

8. The device of claim 7, wherein the peptide is immobilized in the control zone.

9. The device of claim 8, wherein the dried reagent zone comprises an agent conjugated to a detectable label.

* * * * *

UNITED STATES PATENT AND TRADEMARK OFFICE
CERTIFICATE OF CORRECTION

PATENT NO. : 11,237,163 B2
APPLICATION NO. : 16/083486
DATED : February 1, 2022
INVENTOR(S) : Gary et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 354 days.

Signed and Sealed this
Thirteenth Day of December, 2022

*Katherine Kelly Vidal*

Katherine Kelly Vidal
*Director of the United States Patent and Trademark Office*